United States Patent
Lee et al.

[11] Patent Number: 6,022,554
[45] Date of Patent: Feb. 8, 2000

[54] POLYMERIC MICROPOROUS FILM COATED SUBCUTANEOUS IMPLANT

[75] Inventors: Jung-Chung Lee, San Jose; Shamim Pushpala, Sunnyvale; Charles E. Lee, Union City, all of Calif.

[73] Assignee: American Home Products Corporation, Madison, N.J.

[21] Appl. No.: 08/990,367

[22] Filed: Dec. 15, 1997

[51] Int. Cl.$^7$ .................................. A61F 2/00; A61F 2/10
[52] U.S. Cl. .................. 424/423; 424/422; 424/424; 424/425; 424/433; 424/438; 424/468; 424/472; 424/476; 424/484; 424/487; 424/494; 424/498; 530/399
[58] Field of Search ................... 424/422, 423, 424/424, 425, 433, 438, 484, 487, 494, 498, 468, 472, 473, 476; 530/399

[56] References Cited

U.S. PATENT DOCUMENTS

| | | | |
|---|---|---|---|
| 3,948,254 | 4/1976 | Zaffaroni | 128/127 |
| 3,992,518 | 11/1976 | Chien et al. | 424/22 |
| 4,096,239 | 6/1978 | Katz et al. | 424/21 |
| 4,180,560 | 12/1979 | Katz et al. | 424/21 |
| 4,200,098 | 4/1980 | Ayer et al. | 128/260 |
| 4,315,925 | 2/1982 | Hussain et al. | 424/239 |
| 4,333,919 | 6/1982 | Kleber et al. | 424/15 |
| 4,472,394 | 9/1984 | Peterson | 424/243 |
| 4,666,704 | 5/1987 | Shalati et al. | 424/19 |
| 4,758,435 | 7/1988 | Schaaf | 424/425 |
| 5,035,891 | 7/1991 | Runkel et al. | 242/423 |
| 5,091,185 | 2/1992 | Castillo et al. | 424/438 |
| 5,342,622 | 8/1994 | Williams et al. | 424/425 |
| 5,595,762 | 1/1997 | Derrieu et al. | 424/490 |
| 5,618,553 | 4/1997 | Kelleher | 424/428 |

FOREIGN PATENT DOCUMENTS

| | | |
|---|---|---|
| 2 136 688 | 9/1984 | United Kingdom . |
| 2167662 | 6/1986 | United Kingdom . |
| 90 01932 | 3/1990 | WIPO . |

OTHER PUBLICATIONS

International Search Report.
Herschler, R.C. et al., *J. Anim. Sci.*, 73:2873–2881, 1995.
Hsieh, Dean S.T. et al., *Drug Development and Industrial Pharmacy*, 13(15):2651–2666, 1987.
Istasse, L. et al., J. Anim. Sci., 66:1212–1222, 1988.
Ferguson, TH et al., *J. Controlled Release*, 8:45–54, 1988.
Ozturnk, A.G. et al., *J. Controlled Release*, 14:203–213, 1990.
Zhang, X. et al., *J. Controlled Release*, 29:157–161, 1994.
Deasy, P.B. et al., *International J. of Pharmaceutics*, 89:251–259, 1993.
Munday, D.L. et al., *International J. of Pharmaceutics*, 52:109–114, 1989.

(List continued on next page.)

*Primary Examiner*—Thurman K. Page
*Assistant Examiner*—Lakshmi Channavajjala
*Attorney, Agent, or Firm*—Darby & Darby

[57] ABSTRACT

This invention relates to coating formulations for coating sustained-release drug implants. The coating formulations are capable of formulations are capable of forming a porous film coat over a biologically active agent to provide a release of the active agent at a constant rate over a prolonged period of time. The pore forming agent is used in the formulation of the invention in the amount effective to regulate the release of a biologically active compound at a desired rate. Preferably, the effective amount of the pore forming agent provides long term delivery of the active agent. The invention also provides an improved implant for the sustained administration of a biologically active compound suitable for subcutaneous implantation. The invention also relates to methods for making and using the formulation and the implant of the invention.

22 Claims, 18 Drawing Sheets

In Vivo Depletion Study
Depletion of EB through implants containing different concentration of PEG 8000 in the coating film

OTHER PUBLICATIONS

Muhammad, N.A. et al., *Drug Development and Industrial Pharmacy*, 17(18):2497–2509, 1991.

Marini, J.O. et al., *Drug Development and Industrial Pharmacy*, 17(6):865–877, 1991.

Donbrow, M. et al., *J. Pharm. Pharmacol.*, 32:463–470, 1980.

Fed. Regist. (1996), 61(64), 14482, Apr. 2, 1996.

Fed. Regist. (1996) 61(113), 29479–29480, Jun. 11, 1996.

Fed. Regist. (1996), 61(155), 41498–41499, Aug. 9, 1996.

Fed. Regist. (1995), 60(14), 4375–6, Jan. 23, 1995.

Fed. Regist. (1994), 59(189), 49807–8, Sep. 30, 1994.

Zentner, G.M. et al., *J. Pharm. Sci.*, 68(6):794–5, Jun. 1979.

Deasy, P.B. et al., *Proceed. Intern. Symp. Control. Rel. Bioactive Materials*, 20:163–164, 1993.

Coward, P. et al., *J. Virology*, 66(1):286–295, Jan. 1992.

Long Term Release Rate Study

Release of TBA through various levels of coating thickness

Long Term Release Rate Study

Release of EB through various levels of coating thickness

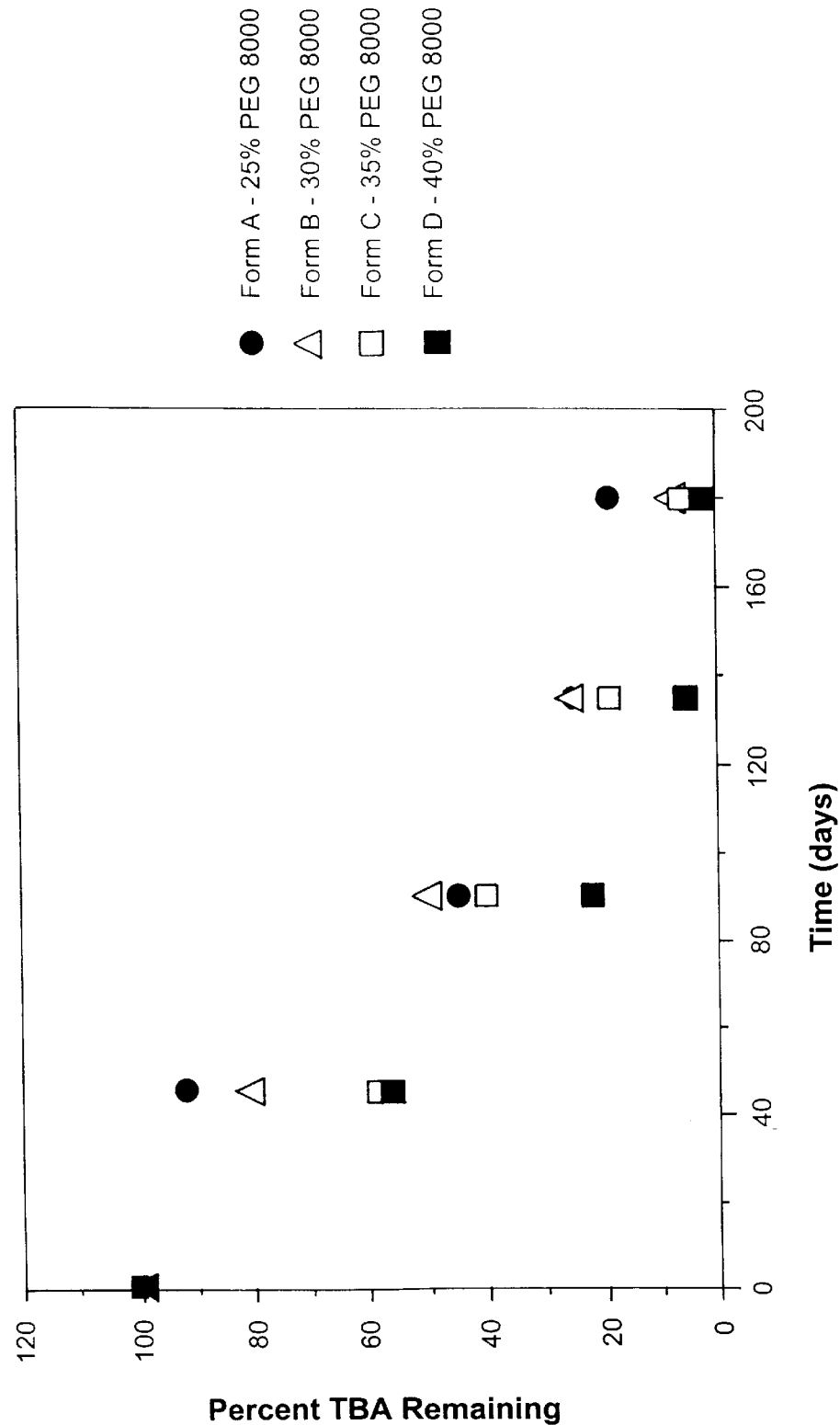

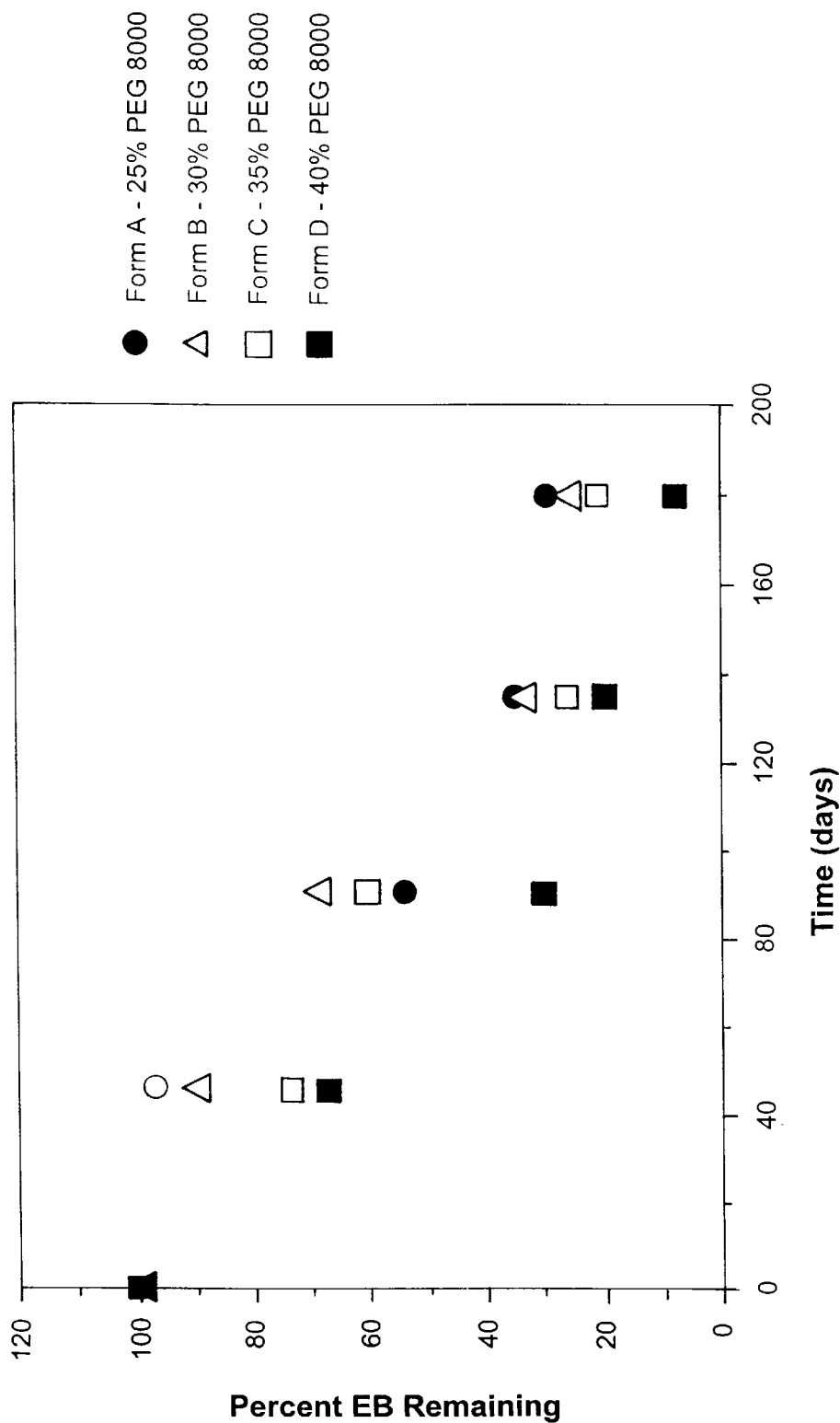

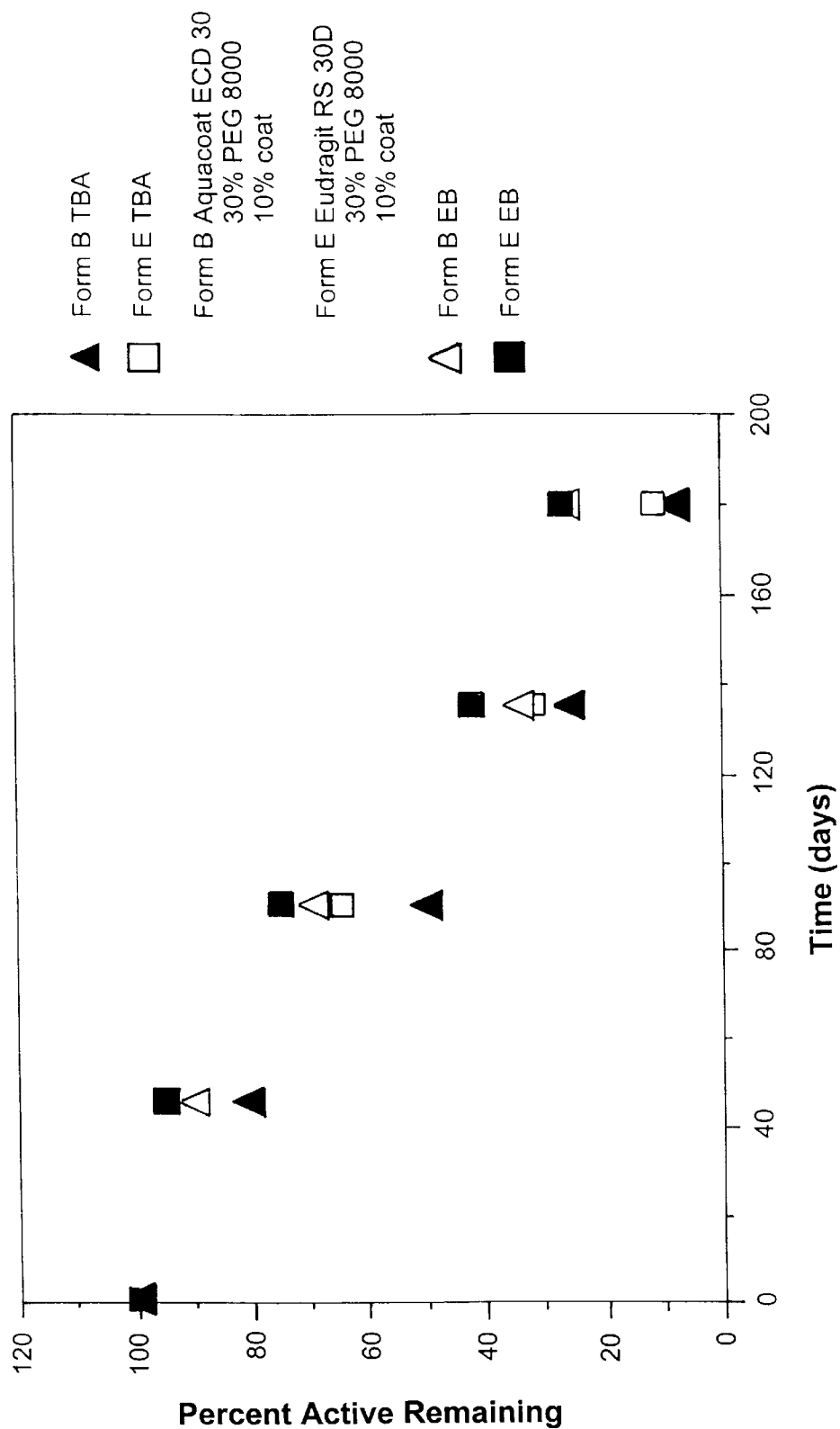

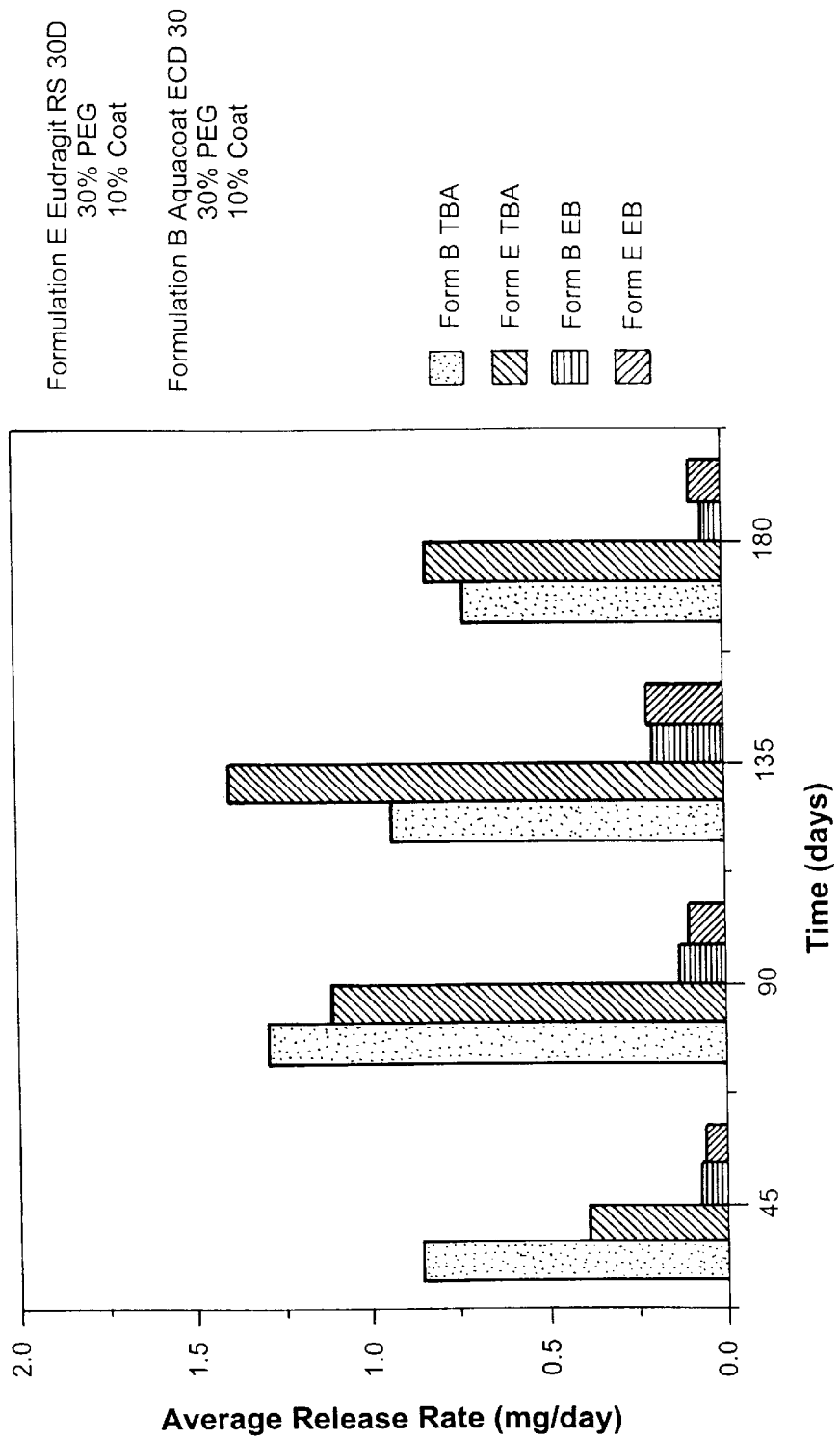

Correlation of In Vitro dissolution of TBA versus PEG 8000 concentration in the coating Correlation of PEG 8000 concentration in the coating versus In Vivo duration of the Implant

POLYMERIC MICROPOROUS FILM COATED SUBCUTANEOUS IMPLANT

FIELD OF THE INVENTION

This invention relates to a novel coating formulation comprising a pore forming agent for use on sustained-release drug implants, an improved implant comprising a biologically active agent and a porous coating film capable of releasing the biologically active agent at a constant rate over a prolonged period of time to produce a local or systemic physiological or pharmacological effect, a method for making an implant coated with the formulation of the invention and a method for using the coated implant to deliver the biologically active agent to a mammal.

BACKGROUND OF THE INVENTION

The advantages of employing sustained-release drug implants are well known in the art. Many therapeutic agents are rapidly metabolized or cleared from the mammalian body requiring frequent administration of the drug to maintain adequate therapeutic concentration. There is therefore a need for a sustained release implant capable of administering an active compound at a relatively constant rate at a level sufficient to maintain an effective concentration.

A number of sustained-release implants are known in the art. Some implants are "matrix" type, and comprise an active compound dispersed in a matrix of a carrier material. The carrier material may be either porous or non-porous, solid or semi-solid, and permeable or impermeable to the active compound. Matrix devices may be biodegradable, i.e., they may slowly erode after administration. Alternatively, matrix devices may be nondegradable, and rely on diffusion of the active compound through the walls or pores of the matrix. Matrix devices may be easily prepared, but are not suitable for all compounds. Furthermore, it is difficult to prepare matrix devices that release active compound at a constant rate (i.e., zero order kinetics). Generally, the release rate is typically a function of the active compound's concentration in the matrix.

U.S. Pat. No. 4,331,651 to Reul discloses a matrix device consisting of a silicone rubber depot for nasal administration to cattle. The rubber contains a "release promoting agent" which is liposoluble, scarcely soluble in water, and which may be an alcohol, ester, ether or ketone of 8–60 carbons. The active compound is a steroid, optionally an antibiotic. Preferred steroids are testosterone and trenbolone acetate, optionally in combination with estrogens such as 17β-estradiol and its derivatives.

Matrix implants are also disclosed in P. J. Dziuk, et al., *Am. J. Vet. Res.* 29, 2413–2417 (1968) "Inhibition and Control of Estrus and Ovulation in Ewes with a Subcutaneous Implant of Silicone Rubber Impregnated with a Progestogen"; L. Beck, et al., *Drugs*, 27, 528–547 (1984) "Controlled-Release Delivery Systems for Hormones"; R. Heitzman, *J. Animal Sci.*, 57, 233–238 (1983) "The Absorption, Distribution and Excretion of Anabolic Agents"; J. Wagner, et al., *J. Animal Sci.*, 58, 1062–67 (1984) "Effect of Monensin, Estradiol Controlled Release Implants and Supplement on Performance in Grazing Steers"; N. Scheffrahn, et al., *J. Animal Sci.*, 51, 108–109, "Induction of Male Sex Behavior in Ewes Using Silastic Implants Containing Testosterone Propionate."

Surface erosion is the major mechanism of delivering the actives to a mammal in a matrix-type implant. By applying a layer of water insoluble film around the implant, the release rate of the actives could be regulated. Such implants are known as "reservoir" type and consist of a central reservoir of active compound surrounded by a rate controlling membrane. This approach requires an adequate diffusion rate of the actives through the membrane.

The membrane may be either porous or non-porous, but is not usually biodegradable. It is typically easier to prepare a reservoir implant capable of zero order kinetics (independent of active compound concentration), as the release rate often depends only on the surface area of the membrane. However, reservoir devices often suffer from an inadequate rate of delivery given that the membrane surface area required to maintain an effective concentration of active compound is frequently so large that it is impractical to administer the implant. Reservoir implants are sensitive to rupture and an excessive, possibly lethal, dose of active compound may be released instantaneously.

Some sustained release devices are hybrids, having a matrix core surrounded by a rate controlling membrane. Other sustained release devices may be mechanical in nature, and include small compound-filled electrical or osmotic pumps. While these devices may be capable of zero order release, they are typically too expensive to compete economically with matrix and reservoir devices.

UK Patent Application 2,010,676 to Wong, et al. discloses a reservoir implant in the form of a flat, heatsealed packet, cylindrical tube or "T" vaginal insert, comprising a rate controlling membrane, specifically ethylene-vinyl acetate copolymer or butylene terephthalate/polytetramethylene ether terephthalate. The active compound is presented in a carrier which is water-imbibing (to maintain, but not increase the size of the implant), and viscous to improve drug distribution within the implant. These implants are useful for administering progesterone, estradiol, or d-norgestrel.

Other reservoir implants are disclosed in L. Beck, et al., "Controlled-Release Delivery Systems for Hormones" *Drugs*, 27, 528–547 (1984); W. Greene et al., "Release Rate of Testosterone and Estrogens from Polydimethylsiloxane Implants for Extended Periods In Vivo Compared with Loss In Vitro" *Int. J. Fertil*, 23, 128–132 (1978); E. Sommerville, et al., "Plasma Testosterone Levels In Adult and Neonatal Female Rats Bearing Testosterone Propionate-Filled Silicone Elastomer Capsules for Varying Periods of Time" *J. Endocr.*, 98, 365–371, (1983); U.S. Pat. Nos. 4,210,644; and 4,432,964.

UK Patent Application 2,154,138A to Roche discloses a hybrid subcutaneous implant for livestock weight promotion, using silicone rubber with estradiol dispersed in the rubber. The implant is formed as a substantially hollow cylinder of the silicone rubber, with a core consisting of active ingredients (which may be steroids) dispersed in a biocompatible, biosoluble polymer which dissolves within days of implantation. The biocompatible, biosoluble polymer is a mixture of high and low molecular weight polyethylene glycol (PEG). For example, PEG 3,000–10,000 can be used with PEG 200–600. Thus, estradiol is released as if from a matrix (the silicone rubber wall), while the second active compound is released from a reservoir.

U.S. Pat. No. 3,992,518 to Chien discloses another hybrid implant comprising a membrane-wrapped silicone rubber matrix. The rubber matrix is prepared by forming an emulsion of rubber monomer and active compound in aqueous solution with a hydrophilic co-solvent, then crosslinking the monomer to form "microsealed compartments" containing the active compound in solution. The resulting matrix is then coated with a rate-controlling membrane. The rate-controlling membrane may be silicone rubber, ethylene/ vinyl acetate, polyethylene terephthalate, butyl rubber, etc. The active compound is in a solution of water and a hydrophilic cosolvent not soluble in the rubber matrix. The hydrophilic cosolvent may be polyethylene glycol, propylene glycol, butylene glycol, etc., with PEG 400 preferred at a concentration of 20–70%. Active compounds disclosed include ethynodiol diacetate, ethylnyl estradiol, estrone, estradiol, other estrogens, progesterone, and testosterone.

U.S. Pat. No. 5,342,622 to Williams et al. discloses a pharmaceutical or veterinary implant comprising a peptide or protein and an excipient encased within a polymeric coating which is permeable and swellable. The coat forms a release rate limiting barrier and is preferably a neutral copolymer based on poly(meth) acrylic acid esters. One such suitable coating is "Eudragit E30D" (available from Rohm Pharma, GmbH).

U.S. Pat. No. 5,091,185 to Castillo et al. discloses a coated veterinary implant comprising a solid core of a growth hormone and a coating of polyvinylalcohol continuously enveloping the core.

U.S. Pat. No. 4,666,704 to Shalati et al. teaches an implant composition comprising (i) a core of a macromolecular drug and a water insoluble polymer and (ii) a pore-forming membrane with uniformly distributed pore-forming agent such as dimethyl and diethyl tartrate and lower partial esters of citric acid.

The mode of administration is usually critical to the design of a sustained release implant. The implant must be adapted to the appropriate biological environment in which it is used. For example, a device for subcutaneous implantation must be non-irritating, mechanically strong to withstand flexion or impact, and should provide long term delivery of the drug. In contrast, a device for oral administration must be designed for resistance to gastric acidity and sensitivity to pH change and short term delivery of drugs. Coatings suitable for gastric environments of acid pH that provide short term delivery of drugs, are known in the art. For example, Munday and Fassihi, *Int. J. Pharm,* 52: 109–114 (1989) disclose an oral control delivery tablet coated with insoluble polymers such as Eudragit RS and RL and a pore forming agent PEG 1540. This coating allows for 100% drug release within 10 hours after administration. Similarly, Marini et al., *Drug Dev. Ind. Pharm,* 17:865–877 (1991) and Muhamed et al., *Drug Dev. Ind. Pharm,* 17:2497–2509 (1991) disclose oral dosage forms comprising a coating with PEG. Both references show that such coating allows drug delivery within hours after administration.

It has now been surprisingly discovered that coatings containing PEG can be successfully used to make long term sustained release drug implants. Such PEG coatings unexpectedly increase the life of implants. For example, most cattle implants on the market have the release duration between 60–90 days. In order to continue promoting the growth of an animal, reimplantation of another dose is essential. R. L. Preston and J. R. Rains, FEEDSTUFFS, January 1993, pp. 18–20. Using implants prepared according to the present invention, the life of implants can be extended to over 150 days thus eliminating the need for repeated implantation. Another advantage of the coating technology of the present invention is that it offers a simple way of extending the duration of an implant without dramatic re-formulation of existing products and excessive costs. A third advantage to the present invention is that by varying amount of pore forming agent, the duration of the implant may be tailored to the desired target.

BRIEF DESCRIPTION OF THE DRAWINGS

FIG. 7a is a graph showing TBA depletion (represented by percent TBA remaining in the implant) depending on varying concentrations of PEG 8000.

FIG. 7c is a graph showing EB depletion (represented by percent EB remaining in the implant) depending on varying PEG 8000 concentrations.

FIG. 9a is a graph showing depletion of actives (represented by percent active remaining) depending on the type of a water insoluble polymer used in the coating.

FIG. 9b is a graph showing depletion of actives (represented by average release rate mg/day) depending on the type of a water insoluble polymer used in the coating.

SUMMARY OF THE INVENTION

Figure 1:
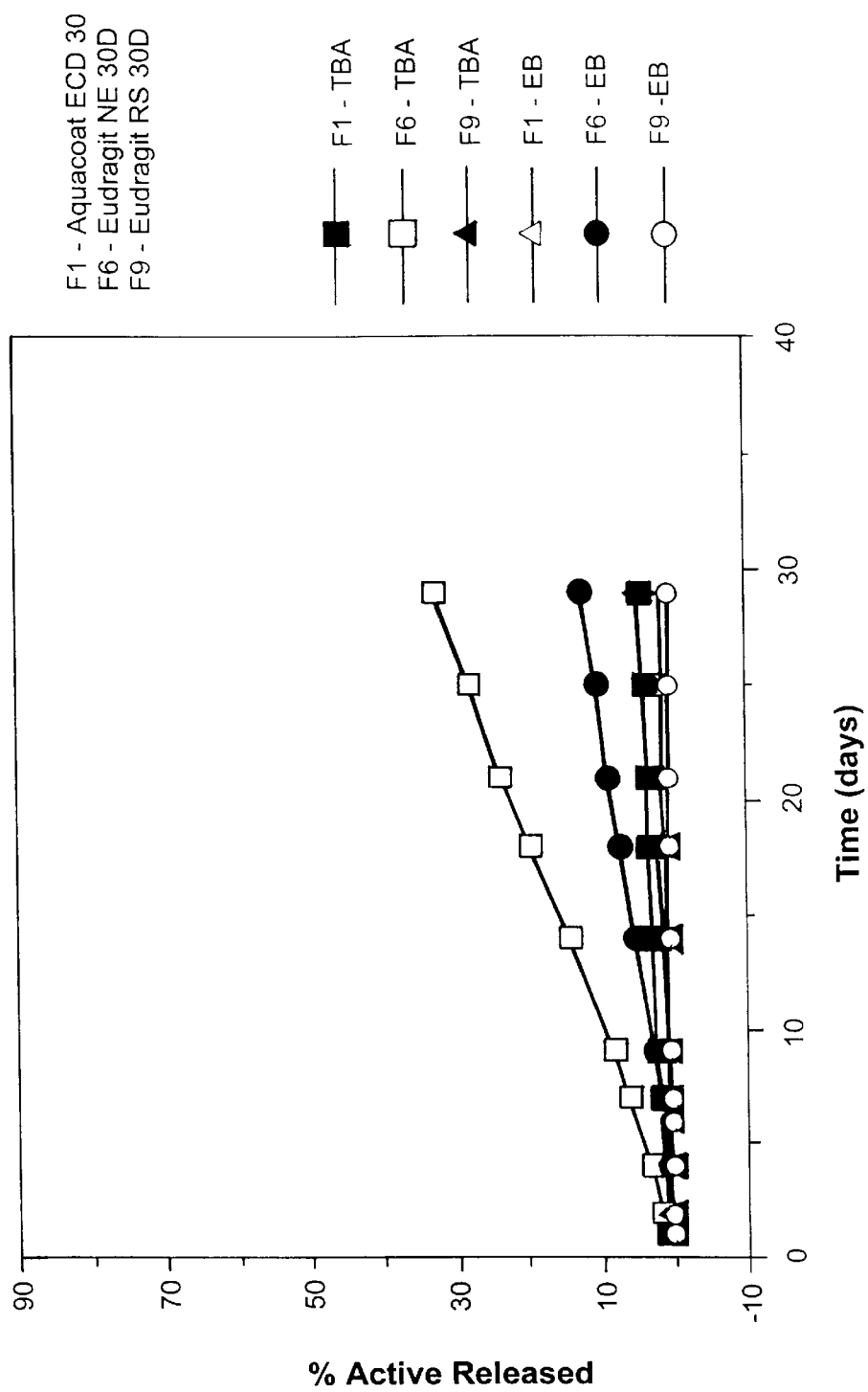
FIG. 1 is a graph showing in vitro diffusion of trenbolone acetate (TBA) and estradiol benzoate (EB) through various polymers.

This invention encompasses novel coating formulations for coating sustained-release drug implants. The coating formulations are capable of forming a porous film over a biologically active agent to provide a release of the active agent at a constant rate over a prolonged period of time. The formulation of the invention comprises a water soluble pore forming agent, such as polyethylene glycol, mixed with a water insoluble polymer. The pore forming agent is used in the formulation of the invention in the amount effective to regulate the release of a biologically active compound at a desired rate. The pore forming agent leaches out through the film in situ, and thus creates a perforated film around the implants which regulates the release rate of actives through micro-channels. Preferably, the effective amount of the pore forming agent provides long term delivery of the active agent.

In another aspect, the invention provides an improved implant for the sustained administration of a biologically active compound, suitable for subcutaneous implantation, which comprises an effective amount of a biologically active agent and a sufficient amount of the porous film coating. The porous film coating comprises a water soluble pore forming agent, such as polyethylene glycol, and water insoluble polymers and is prepared by coating the biologically active compound with the formulation of the invention. The porous film comprises the pore forming agent in the amount effective to increase the useful life of the implant.

In a further aspect, the invention provides for a method for making the formulation and the implant of the invention.

In yet another aspect, the invention provides for a method of treating a mammal by implanting the improved implant of the invention.

DETAILED DESCRIPTION OF THE INVENTION

All patent applications, patents, and literature references cited in this specification are hereby incorporated by reference in their entirety. In the case of inconsistencies, the present description, including definitions, will control.
Definitions The term "biologically active compound" as used herein refers to a compound useful for effecting some beneficial change in the subject to which it is administered. For example, "biologically active compounds" within the scope of this definition include steroid hormones, prostaglandins, vitamins, antibiotics, antiinflammatory agents, chemotherapeutic agents, cardiovascular and antihypertensive agents. Preferred biologically active compounds within the invention are steroid hormones useful for promoting weight gain in livestock, especially estradiol benzoate, trenbolone acetate, progesterone, and testosterone propionate.

The term "pharmaceutically acceptable steroid" refers to a steroid hormone suitable for parenteral administration to a mammal, particularly a human. Suitable steroids include levonorgestrel, estradiol 17β-, testosterone, testosterone propionate, and ethinyl estradiol.

The term "effective amount" as applied to the biologically active compound refers to that amount which is sufficient to effect the desired change in the subject. For example, where the desired effect is an increase in weight gain of livestock, the "effective amount" is a "livestock weight gain-promoting" amount, and will vary depending on the animal species. If the desired effect is human contraception, an effective amount is that amount sufficient to result in contraception, which can be easily determined by one of ordinary skill in the art.

The term "effective amount" as applied to the pore forming agent refers to that amount which is sufficient to regulate the release of a biologically active agent at a desired rate for a desired period of time. For example, where the desired effect is an increase in weight gain of livestock by using a single implant during the productive cycle, the "effective amount" is the amount that will extend the release over a period of more than 150 days. This "effective amount" can be determined based on the teaching in this specification and the general knowledge in the art.

The term "sufficient amount" as applied to the coating film formulation refers to the amount of surface area of membrane required to effect a flux of biologically active compound sufficient to achieve the desired purpose. The area necessary may be determined and adjusted directly by measuring the release obtained for the particular active compound. The surface area of the coating is that amount of membrane necessary to completely encapsulate the biologically active compound. The surface area depends on the geometry of the implant. Preferably, the surface area is minimized where possible, to reduce the size of the implant. In one preferred embodiment of the invention, suitable for implantation in cattle, the implant device is a cylinder measuring approximately 3.2 mm by 30.5 mm and having a surface area of 3.227 cm$^2$.

The term "treatment" as used herein covers any treatment of a disease in an animal (including a human), and includes: (i) preventing the disease from occurring; (ii) inhibiting the disease, i.e., arresting its development; (iii) relieving the disease, i.e., causing regression of the disease; or (iv) modifying normal biological activity such as in the case of promotion of weight gain or contraception.

The present invention provides novel coating formulations for coating sustained-release drug implants. The coating formulations are capable of forming a porous film over a biologically active agent to provide release of the active agent at a constant rate over a prolonged period of time. The formulation of the invention comprises a water soluble pore forming agent, such as polyethylene glycol, mixed with water insoluble polymers.

The water soluble pore forming agent is preferably polyethylene glycol. Other water soluble pore forming agents can also be used, for example, polypropylene glycol, sugars (lactose, sucrose, dextrose, etc.), salt, poloxamers, polyvinyl alcohol and other water soluble food grade and other excipients. When PEG is used as a pore forming agent of the invention, the molecular weight of PEG is in the range from about 200 to about 20,000, preferably from about 540 to about 8,000. Most preferably, PEG having a molecular weight of about 1,000 to about 8,000 is used. In another preferred embodiment, PEG has a molecular weight of about or above 4,000 to about 8,000.

The molecular weight of PEG used for the coating formulation of the invention will depend on the ability of PEG to form a coating film that is non-sticky, having enough strength and creating adequate pore size for controlling the release of actives in both in vitro and in vivo.

The pore forming agent is used in the formulation of the invention in the amount effective to regulate the release of a biologically active compound at a desired rate. Preferably, the effective amount of the pore forming agent provides long term delivery of the active agent thus increasing the useful life of a sustained-release drug implant. The effective amount of the pore forming agent will depend on the desired rate and duration of the release and the ability to form a continuous microporous film during the coating process.

In one of the presently preferred embodiments, the coating formulation of the invention is used to coat pellets comprising steroids administered for the purpose of increasing weight gain. To enable release duration over a period longer than 100 days, PEG 8000, for example, is used in a concentration from 10 to 50%, preferably from 20 to 45% and most preferably from 30 to 45%. The concentration of PEG is expressed herein in % weight per dry basis and represents the concentration of PEG in the coating film after drying. Similarly, the thickness of the coating film is from 5 to 50 µm, preferably 30 from 10 to 30 µm and most preferably from 15 to 25 µm.

There is a good correlation between the dissolution rate of active agents and the amount of pore forming agent incorporated in the coating film based on in vitro and in vivo studies shown in the Examples. Depending on the desired length of release, the PEG concentration ranges can be adjusted using correlation coefficients provided in the Examples. For example, in vivo duration of a coated implant may be predicted simply from the in vitro dissolution rate of the active agent at the 120-hour time point. Using the coating formulation of this invention, it is possible to prolong the 100-day duration of implants currently available on the market to a desired, longer duration of 150, 180 or 200 days.

In a presently most preferred embodiment of the invention, the coating formulation enables release of steroids over a period of over 200 days. In this case, the concentration of PEG is from 10 to 50%, preferably from 20 to 40% and most preferably from 30 to 40%. One such desirable coating formulation for a 200-day duration was determined to comprise the Aquacoat ECD 30 polymers (registered trademark of FMC Corporation) with 30% PEG and 15 % overall coating. The chemical composition of this polymer is disclosed in the Examples.

The coating formulation of the invention also comprises a water insoluble polymer. Examples of such polymers are ethylcellulose, acrylic resins, co-polymer of methacrylic acid and acylic acid ethyl ester, polylactic acid, PLGA, polyurethane, polyethylene vinyl acetate copolymer, polystyrene-butadiene copolymer and silicone rubber, or mixtures thereof. Preferably, the polymers sold under tradenames Aquacoat ECD 30 and Eudragit RS 30 and NE 30D (registered trademarks of Rhom Tech, Inc.) are used. The chemical composition of these polymers is disclosed in the Examples.

A polymer suitable for use in this invention is a polymer which is capable of forming a continuous coating film during the process of spraying and drying with a pore forming agent. The rate controlling film prepared with such a polymer is very stable during implantation. The film should have enough strength to withstand tear and inner osmotic pressure, and have the stability not to swell or hydrate during the implantation life.

The coating formulation of the invention may be coated over a biologically active compound by methods generally known in the art. For example, the coating formulation may be sprayed onto pellets containing a biologically active agent until desired coat thickness is achieved and then cured in the oven at from 40–60° C. or at the curing conditions recommended by the polymer supplier. The coat thickness will be from 5 to 50 µm, preferably from 10 to 30 µm and most preferably from 15 to 25 µm. Coating methods described in the U.S. Pat. No: 5,035,891 can also be used.

Another aspect of the invention is an improved implant for sustained administration of a biologically active compound, suitable for subcutaneous implantation which comprises an effective amount of a biologically active compound and a sufficient amount of a porous coating film which completely encapsulates said biologically active compound. In a preferred embodiment, the implant of the invention comprises the biologically active compound in the form of a pellet or a plurality of pellets, for example three to fifteen pellets. An implant in which said biologically active agent comprises an estrogen derivative in combination with a progestogen or an androgenic agent is also preferred. More preferably, said estrogen derivative is estradiol benzoate, particularly where the estradiol benzoate is in combination with progesterone, testosterone propionate, or trenbolone acetate. One of the preferred embodiments is an improved implant comprising estradiol benzoate and trenbolone acetate for long term delivery having a lifetime duration over 100 days and preferably over 180+ days.

The manufacture of an implant of the invention may be accomplished through a variety of methods known in the art, for example those disclosed in the U.S. Pat. No. 5,035,891.

This invention also provides for an improved implant further comprising an amount of an antibiotic present within the solid formulation or on the outer surface of the porous coating film in an amount sufficient to prevent infection associated with implantation of said implant. Such antibiotic may be applied to the implant by methods known in the art, and for example as disclosed in U.K. Application No: 2,136,688A to Ferguson.

The amount of a biologically active compound in the improved implant of the invention may be as is commonly known and used in the art. For example, steroid containing pellets can contain the amount disclosed in the U.S. Pat. No. 5,035,891 to Runkel et al. According to one of the embodiments of the invention, an implant may comprise eight pellets comprising a total of 28 mg estradiol benzoate and 200 mg trenbolone acetate. According to another embodiment, an implant containing a porous coating film of the invention may comprise six pellets and a total of 24 mg estradiol and 120 mg trenbolone acetate.

It is within the knowledge and skill of those skilled in the art to determine the amount of an active agent used in the implant. Generally, the amount of a biologically active compound administered via the implant of the invention will vary depending on the identity of the compound; the size, age, weight, and species of the subject to be treated; the severity of the condition or the magnitude of the effect desired, and so forth. These parameters are easily determined and factored by one of ordinary skill in the art. For example, a representative implant of the invention suitable for promoting growth in steers contains a combination of about 200 mg of progesterone and about 20 mg of estradiol benzoate as the biologically active compound. A representative implant suitable for promoting growth in heifers contains a combination of about 200 mg of testosterone propionate and about 20 mg estradiol benzoate as the biologically active compound.

Another aspect of the invention is a method for administering a biologically active compound to a subject in need thereof over an extended time period which comprises implanting subcutaneously the implant of the invention. One of preferred embodiments of the invention is the method that comprises subcutaneously administering an implant comprising an effective amount of a weight gain promoting steroid, and a sufficient amount of a porous coating film of the invention. In another preferred method, an implant comprising a pellet or plurality of pellets comprising 20–1,000 mg of progesteronne, testosterone propionate, or trenbolone acetate, 2–100 mg of estradiol benzoate, 3.23 cm$^2$ of a porous film comprising PEG 8000 as a pore forming agent.

An improved implant of the invention which is administered to promote growth in cattle may be implanted subcutaneously using a hollow needle implanting gun, for example the type disclosed in U.S. Pat. No. 4,474,572, incorporated herein by reference. The diameter of the needle may be adjusted to correspond to the size of the implant used. For administration to cattle, the implant is placed subcutaneously in the middle third of the subject's ear.

Alternative sites of subcutaneous administration include the nape of the subject's neck and the axillary region. Other devices of the invention, when scaled to a suitable size, are suitable for similar implantation in sheep, swine or horses.

Another aspect of the invention is a method for administering a pharmaceutically acceptable steroid to a mammal to effect contraception, estrogen replacement therapy, or breast cancer treatment, which method comprises subcutaneously implanting a reservoir implant comprising an effective amount of a pharmaceutically acceptable steroid. Another embodiment of the invention comprises a contraceptive or chemotherapeutic implant for humans. The microporous film suitable for use in humans comprise bio-erodible polymers such as high molecular weight PLGA or orthoesters.

The sustained-release implants of the invention are designed for subcutaneous implantation, but may alternatively be administered to other body cavities, for example, vaginally, nasally and sublingually.

Pharmaceutical excipient can also be used in the implants of the invention. Suitable excipient are well known in the art and include starch, cellulose, talc, glucose, lactose, sucrose, gelatin, malt, rice, flour, chalk, silica gel, magnesium stearate, sodium stearate, glycerol monostearate, sodium chloride and dried skim milk.

EXAMPLES

Various subcutaneous implants containing trenbolone acetate (TBA) and estradiol benzoate (EB) as biologically active agents coated with a polymeric microporous film of the invention were prepared and tested in vitro and in vivo to determine the duration and rate of release of active agents. A good correlation between the release rate of actives, i.e., TBA and EB, duration of the implant and amount of PEG 8000 incorporated in the film coating was observed.

Formulation of Test Coating Films

All implants used in the experiment consisted of 8 pellets, each comprising 25 mg TBA and 3.5 mg EB. Each implant was coated with a layer of a polymeric film. Two sets of film formulations (designated F1–F10 and A–F) were prepared from Aquacoat® and Eudragit® aqueous dispersions with Polyethylene Glycol (PEG) 8000 as a pore forming agent. The percentage of ingredients in each film formulation were as outlined in the following Table A.

In Table A, Aquacoat ECD30, a registered trademark of FMC Corporation, is a water dispersion of 24.5–29.5% cellulose ethyl ether; 0.9–1.7% sodium lauryl sulfate; and 1.7–3.3% cetyl alcohol.

Eudragit™ RS 30D, a registered trademark of Rhom Tech, Inc., is a polymer synthesized from acrylic and methacrylic acid esters with a low content of quaternary ammonium groups. It is a water dispersion of 29–32% of poly (ethylacrylate, methylmethacrylate, trimethylammonioethylmethacrylate chloride) in the ratio 1:2:0.1. To form a microporous film using this grade of Eudragit, 20% of triethyl citrate was used as a plasticizer. Other plasticizers, for example dibutyl sebecate, can also be used.

The Eudragit™ NE 30D is about 30% aqueous dispersion of a neutral polymerization product based on poly(meth) acrylic acid esters. No plasticizer is needed when this grade of Eudragit™ is used to prepare microporous films.

PEG 8000 is polyethylene glycol having a molecular weight (MW) of about 8,000. Talc (hydrous magnesium silicate) is used as a filler and detacking agent.

Preparation of Coating Suspensions and Coating of Pellets

Coating suspensions were prepared from the above polymeric dispersions according to the following steps: (1) screening the resin dispersion through a 60-mesh screen to break the big lumps, if any; (2) weighing the required amount of the screened dispersion and adding a required amount of plasticizer, if needed, and mixing for 20 minutes using a Lightning mixer; (3) dissolving the required amount of PEG 8000 in water and adding to the coating dispersion, mixing for 2 minutes and then passing the final dispersion through a 60-mesh screen; (4) charging the pellets into table top perforated coating pan with vacuum and dryer on; (5) rotating the pan at a set speed and spraying the coating dispersion at the set air pressure and spray rate; (6) sampling the coated pellets to monitor the weight gain (the spraying is stopped when desired weight gain is achieved); and (7) drying the pellets for few minutes and subsequently curing the coating.

In vitro Long Term Release Rate Study

The TBA and EB long term release rates from implants coated with test film formulations were determined in vitro. Ten film coating formulations designated F1 to F10 in the above table were used for this study. As indicated, the coating formulations consisted of aqueous polymer disper-

TABLE A

| | AQUACOAT ECD 30 | Eudragit NE 30D | Eudragit RS 30D | Dibutyl Sebecate | Triethyl citrate | Talc | PEG 8000 | Total Coating (% w/w) |
|---|---|---|---|---|---|---|---|---|
| F1 | 80% | | | 20% | | | | 5% |
| F2 | 72% | | | 18% | | | 10% | 5% |
| F3 | 56% | | | 14% | | | 30% | 5% |
| F4 | 48% | | | 12% | | | 40% | 5% |
| F5 | 56% | | | 14% | | | 30% | 10% |
| F6 | | 100% | | | | | | 5% |
| F7 | | 70% | | | | | 30% | 5% |
| F8 | | 70% | | | | | 30% | 10% |
| F9 | | | 45% | | 9.1% | 45% | | 5% |
| F10 | | | 32% | | 6.4% | 32% | 30% | 5% |
| A | 60% | | | 15% | | | 25% | 10% |
| B | 56% | | | 14% | | | 30% | 10% |
| C | 52% | | | 13% | | | 35% | 10% |
| D | 48% | | | 12% | | | 40% | 10% |
| E | | | 32% | | 6.4% | 32% | 30% | 10% |
| F | 52% | | | 13% | | | 35% | 15% | sions (such as Aquacoat ECD 30, Eudragit NE 30D or Eudragit RS 30D) mixed with PEG 8000, a pore forming agent. The concentration of PEG 8000 was in the range from 0–40%. A thin coat comprising 5% and a medium thick coat comprising 10% by weight of an implant were also tested to evaluate the integrity of the coating film during the period of the TBA and EB release.

Pellets coated with film formulations F1 to F10 were placed in a reciprocating apparatus (similar to USP-4 dissolution apparatus) for 29 days and the release of TBA and EB was monitored. Four pellets per each formulation were used for dissolution testing. They were placed in the basket attached to the rods. The stroke speed for the rods was adjusted to 30 strokes/min. The bath temperature was maintained at 37° C. and the release media used was 3% bile salt in purified water.

Samples were collected at time intervals indicated in Tables 1 and 2, and the amount of TBA and EB released was determined using HPLC. The HPLC operating conditions were as follows: 1) the column was Brownlee's MPLC RP-18 column fitted with a 3 cm guard column; 2) the mobile phase was acetonitrile: water (60:40) mixture; 3) the flow rate was: 2 ml/min; and 4) the detector was set at UV wavelength 231 nm. The TBA and EB retention times were 3.5 and 10.2 minutes, respectively.

The average cumulative release and the release rate for both TBA and EB in this study are represented in Tables 1 and 2.

As illustrated in FIG. 1, coating films composed of Aquacoat ECD 30 or Eudragit RS 30D with 0% PEG 8000 prevent release of both TBA and EB. In contrast, Eudragit NE 30D permits some transport of both active agents through the membrane even in the absence of a pore forming agent.

Figure 2:
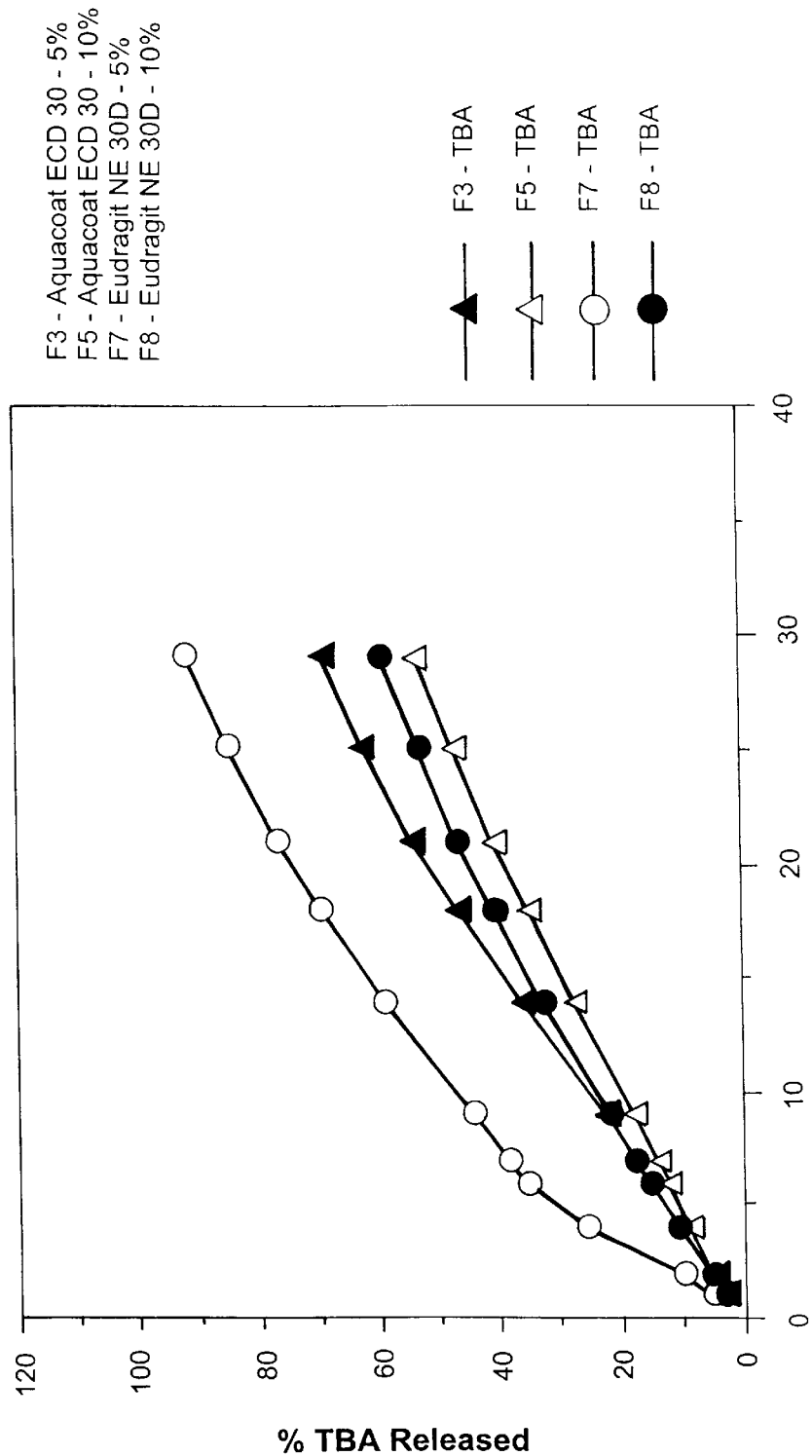
FIG. 2 is a graph showing in vitro release of TBA (%) across various levels of coating thickness.
Figure 3:
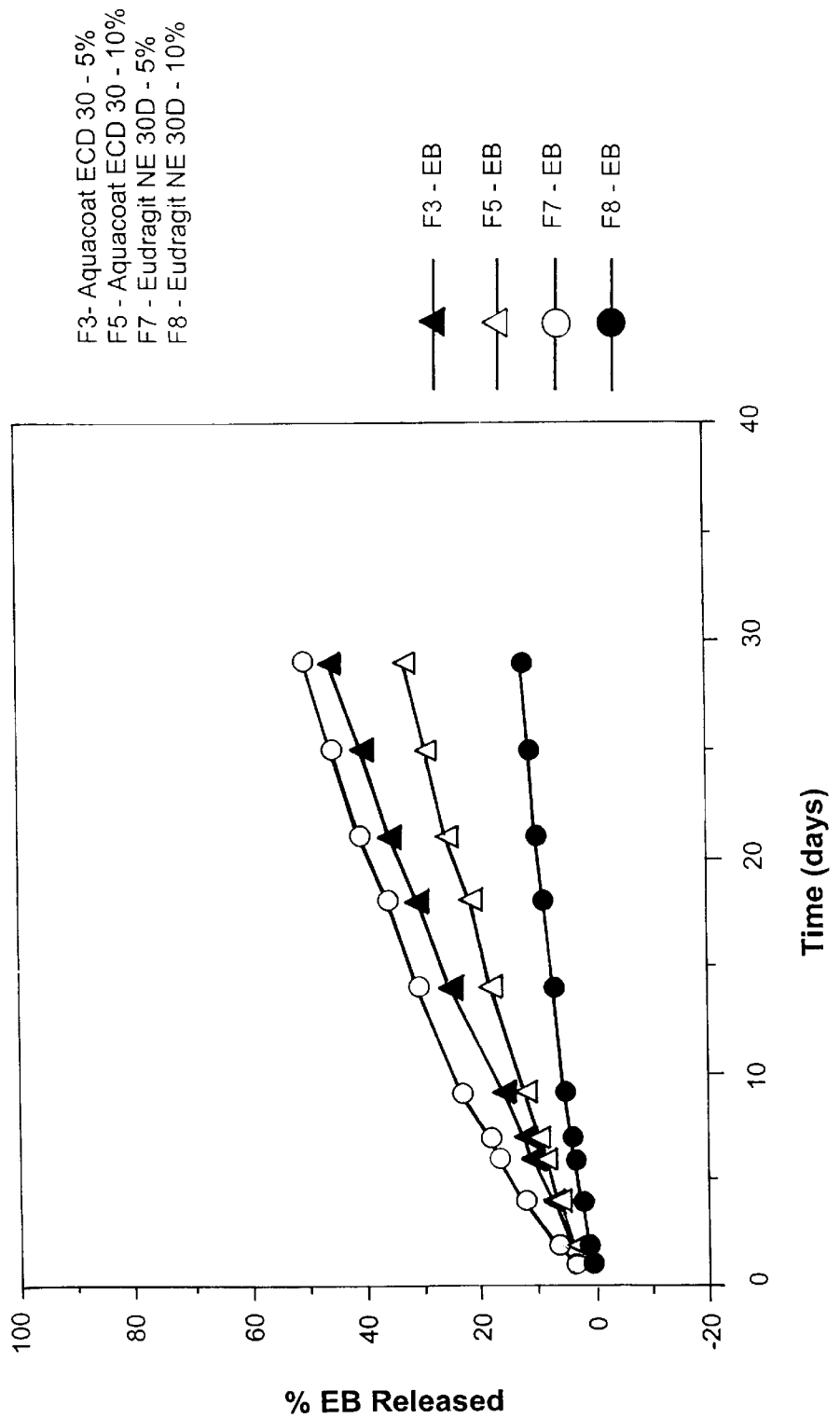
FIG. 3 is a graph showing in vitro release of EB across various levels of coating thickness.

The results show that the thickness of the coating (5% versus 10%) affects the permeability for the actives. FIGS. 2 and 3 represent data for TBA and EB cumulative release at two tested coating thicknesses. The thicker coating slows down the release rate of both actives. This is likely a result of the smaller tortuosity of pore channels created in a thicker film. It is expected, however, that the effect of thickness will be minimal when a certain thickness is reached.

TABLE 1

AVERAGE IN VITRO CUMULATIVE RELEASE (%) AND RELEASE RATE (MG/DAY) OF TRENBOLONE ACETATE FROM VARIOUS LONG ACTING TBA/EB PREPARATIONS

| F# | COATING POLYMER | % PEG | % COAT | RELEASE TIME (DAYS) | | | | | | | | | | |
|---|---|---|---|---|---|---|---|---|---|---|---|---|---|---|
| | | | | 1 | 2 | 4 | 6 | 7 | 9 | 14 | 18 | 21 | 25 | 29 |
| AVERAGE CUMULATIVE RELEASE (%) OF TBA | | | | | | | | | | | | | | |
| F1 | AQUACOAT ® ECD 30 | 0.0 | 5.0 | 1.01 | 1.15 | 1.38 | 1.38 | 1.72 | 1.92 | 2.44 | 2.90 | 3.23 | 3.64 | 4.21 |
| F2 | AQUACOAT ® ECD 30 | 10.0 | 5.0 | 1.12 | 1.35 | 1.74 | 1.74 | 2.23 | 2.57 | 3.51 | 4.14 | 5.26 | 6.72 | 7.89 |
| F3 | AQUACOAT ® ECD 30 | 30.0 | 5.0 | 3.15 | 5.47 | 9.87 | 15.34 | 17.52 | 22.38 | 36.22 | 46.36 | 54.12 | 62.07 | 69.14 |
| F4 | AQUACOAT ® ECD 30 | 40.0 | 5.0 | 7.37 | 14.70 | 27.86 | 40.47 | 45.12 | 54.42 | 72.57 | 83.20 | 89.38 | 94.40 | 96.43 |
| F5 | AQUACOAT ® ECD 30 | 30.0 | 10.0 | 3.12 | 4.95 | 8.65 | 12.49 | 14.13 | 17.70 | 27.33 | 35.07 | 40.71 | 47.31 | 53.81 |
| F6 | EUDRAGIT ® NE 30D | 0.0 | 5.0 | 0.71 | 1.41 | 3.11 | 3.11 | 5.92 | 8.04 | 14.02 | 19.27 | 23.03 | 27.59 | 32.06 |
| F7 | EUDRAGIT ® NE 30D | 30.0 | 5.0 | 5.17 | 9.84 | 25.61 | 35.51 | 38.39 | 44.48 | 58.92 | 69.40 | 76.59 | 84.72 | 91.70 |
| F8 | EUDRAGIT ® NE 30D | 30.0 | 10.0 | 2.85 | 5.45 | 10.34 | 15.14 | 17.22 | 21.35 | 32.42 | 40.75 | 46.38 | 53.05 | 59.16 |
| F9 | EUDRAGIT ® RS 30D | 0.0 | 5.0 | 0.05 | 0.11 | 0.21 | 0.21 | 0.44 | 0.64 | 1.32 | 2.05 | 2.65 | 3.56 | 4.48 |
| F10 | EUDRAGIT ® RS 30D | 30.0 | 5.0 | 2.78 | 5.51 | 10.51 | 15.37 | 17.24 | 21.41 | 32.59 | 41.07 | 46.93 | 54.42 | 61.01 |
| AVERAGE RELEASE RATE (MG/DAY) OF TBA | | | | | | | | | | | | | | |
| F1 | AQUACOAT ® ECD 30 | 0.0 | 5.0 | 1.01 | 0.16 | 0.11 | 0.00 | 0.11 | 0.10 | 0.11 | 0.12 | 0.11 | 0.10 | 0.14 |
| F2 | AQUACOAT ® ECD 30 | 10.0 | 5.0 | 1.13 | 0.23 | 0.20 | 0.00 | 0.17 | 0.17 | 0.19 | 0.16 | 0.38 | 0.37 | 0.30 |
| F3 | AQUACOAT ® ECD 30 | 30.0 | 5.0 | 3.19 | 2.35 | 2.23 | 2.77 | 2.21 | 2.46 | 2.81 | 2.57 | 2.62 | 2.02 | 1.79 |
| F4 | AQUACOAT ® ECD 30 | 40.0 | 5.0 | 7.46 | 7.43 | 6.66 | 6.38 | 4.71 | 4.71 | 3.68 | 2.69 | 2.08 | 1.27 | 0.52 |
| F5 | AQUACOAT ® ECD 30 | 30.0 | 10.0 | 3.12 | 1.84 | 1.85 | 1.92 | 1.64 | 1.79 | 1.93 | 1.94 | 1.89 | 1.66 | 1.63 |
| F6 | EUDRAGIT ® NE 30D | 0.0 | 5.0 | 0.72 | 0.70 | 0.86 | 0.00 | 0.95 | 1.08 | 1.21 | 1.33 | 1.27 | 1.16 | 1.14 |
| F7 | EUDRAGIT ® NE 30D | 30.0 | 5.0 | 5.21 | 4.71 | 7.96 | 4.99 | 2.91 | 3.28 | 2.83 | 2.64 | 2.42 | 2.05 | 1.76 |
| F8 | EUDRAGIT ® NE 30D | 30.0 | 10.0 | 2.85 | 2.60 | 2.44 | 2.40 | 2.08 | 2.07 | 2.21 | 2.08 | 1.88 | 1.67 | 1.53 |
| F9 | EUDRAGIT ® RS 30D | 0.0 | 5.0 | 0.05 | 0.05 | 0.06 | 0.00 | 0.07 | 0.10 | 0.14 | 0.18 | 0.20 | 0.23 | 0.23 |
| F10 | EUDRAGIT ® RS 30D | 30.0 | 5.0 | 2.80 | 2.76 | 2.52 | 2.46 | 1.89 | 2.10 | 2.25 | 2.14 | 1.97 | 1.89 | 1.66 |

TABLE 2

AVERAGE IN VITRO CUMULATIVE RELEASE (%) AND RELEASE RATE (MG/DAY)
OF ESTRADIOL BENZOATE FROM VARIOUS LONG ACTING TBA/EB PREPARATIONS

| F# | COATING POLYMER | % PEG | % COAT | 1 | 2 | 4 | 6 | 7 | 9 | 14 | 18 | 21 | 25 | 29 |
|---|---|---|---|---|---|---|---|---|---|---|---|---|---|---|
| AVERAGE CUMULATIVE RELEASE (%) OF EB | | | | | | | | | | | | | | |
| F1 | AQUACOAT ® ECD 30 | 0.0 | 5.0 | 0.67 | 0.67 | 0.67 | 0.67 | 0.67 | 0.67 | 0.67 | 0.81 | 0.94 | 1.06 | 1.30 |
| F2 | AQUACOAT ® ECD 30 | 10.0 | 5.0 | 0.89 | 0.89 | 0.89 | 0.89 | 1.01 | 10.01 | 1.34 | 1.48 | 2.03 | 2.77 | 3.35 |
| F3 | AQUACOAT ® ECD 30 | 30.0 | 5.0 | 2.34 | 3.89 | 6.98 | 10.76 | 12.29 | 15.69 | 24.87 | 30.69 | 35.61 | 40.16 | 45.01 |
| F4 | AQUACOAT ® ECD 30 | 40.0 | 5.0 | 5.18 | 10.61 | 20.86 | 30.56 | 31.21 | 41.69 | 54.91 | 62.22 | 68.04 | 72.77 | 76.60 |
| F5 | AQUACOAT ® ECD 30 | 30.0 | 10.0 | 2.32 | 3.47 | 5.98 | 8.54 | 9.72 | 12.14 | 17.58 | 21.64 | 25.25 | 28.73 | 32.44 |
| F6 | EUDRAGIT ® NE 30D | 0.0 | 5.0 | 0.04 | 0.09 | 0.57 | 0.57 | 1.67 | 2.56 | 5.11 | 6.92 | 8.49 | 10.11 | 12.01 |
| F7 | EUDRAGIT ® NE 30D | 30.0 | 5.0 | 3.02 | 5.93 | 11.77 | 16.82 | 18.68 | 22.97 | 30.51 | 36.01 | 40.61 | 45.13 | 49.71 |
| F8 | EUDRAGIT ® NE 30D | 30.0 | 10.0 | 0.61 | 1.19 | 2.31 | 3.37 | 3.83 | 4.76 | 6.97 | 8.42 | 9.63 | 10.83 | 12.23 |
| F9 | EUDRAGIT ® RS 30D | 0.0 | 5.0 | 0.00 | 0.00 | 0.00 | 0.00 | 0.00 | 0.00 | 0.00 | 0.00 | 0.00 | 0.00 | 0.00 |
| F10 | EUDRAGIT ® RS 30D | 30.0 | 5.0 | 0.61 | 1.19 | 2.31 | 3.34 | 3.74 | 4.71 | 6.63 | 8.06 | 9.34 | 10.69 | 12.06 |
| AVERAGE RELEASE RATE (MG/DAY) OF EB | | | | | | | | | | | | | | |
| F1 | AQUACOAT ® ECD 30 | 0.0 | 5.0 | 0.09 | 0.00 | 0.00 | 0.00 | 0.00 | 0.00 | 0.00 | 0.00 | 0.01 | 0.00 | 0.01 |
| F2 | AQUACOAT ® ECD 30 | 10.0 | 5.0 | 0.13 | 0.00 | 0.00 | 0.00 | 0.01 | 0.00 | 0.01 | 0.00 | 0.03 | 0.03 | 0.02 |
| F3 | AQUACOAT ® ECD 30 | 30.0 | 5.0 | 0.33 | 0.22 | 0.22 | 0.27 | 0.22 | 0.24 | 0.26 | 0.21 | 0.23 | 0.16 | 0.17 |
| F4 | AQUACOAT ® ECD 30 | 40.0 | 5.0 | 0.74 | 0.77 | 0.73 | 0.89 | 0.52 | 0.53 | 0.37 | 0.28 | 0.28 | 0.17 | 0.14 |
| F5 | AQUACOAT ® ECD 30 | 30.0 | 10.0 | 0.33 | 0.16 | 0.18 | 0.18 | 0.16 | 0.17 | 0.15 | 0.14 | 0.17 | 0.12 | 0.13 |
| F6 | EUDRAGIT ® NE 30D | 0.0 | 5.0 | 0.0t | 0.01 | 0.03 | 0.00 | 0.05 | 0.06 | 0.07 | 0.06 | 0.07 | 0.06 | 0.07 |
| F7 | EUDRAGIT ® NE 30D | 30.0 | 5.0 | 0.43 | 0.41 | 0.41 | 0.36 | 0.26 | 0.30 | 0.21 | 0.19 | 0.22 | 0.16 | 0.16 |
| F8 | EUDRAGIT ® NE 30D | 30.0 | 10.0 | 0;08 | 0.08 | 0.08 | 0.07 | 0.06 | 0.07 | 0.06 | 0.05 | 0.06 | 0.04 | 0.05 |
| F9 | EUDRAGIT ® RS 30D | 0.0 | 5.0 | 0.00 | 0.00 | 0.00 | 0.00 | 0.00 | 0.00 | 0.00 | 0.00 | 0.00 | 0.00 | 0.00 |
| F10 | EUDRAGIT ® RS 30D | 30.0 | 5.0 | 0.08 | 0.08 | 0.08 | 0.07 | 0.06 | 0.07 | 0.05 | 0.05 | 0.06 | 0.05 | 0.05 |

Figure 4:
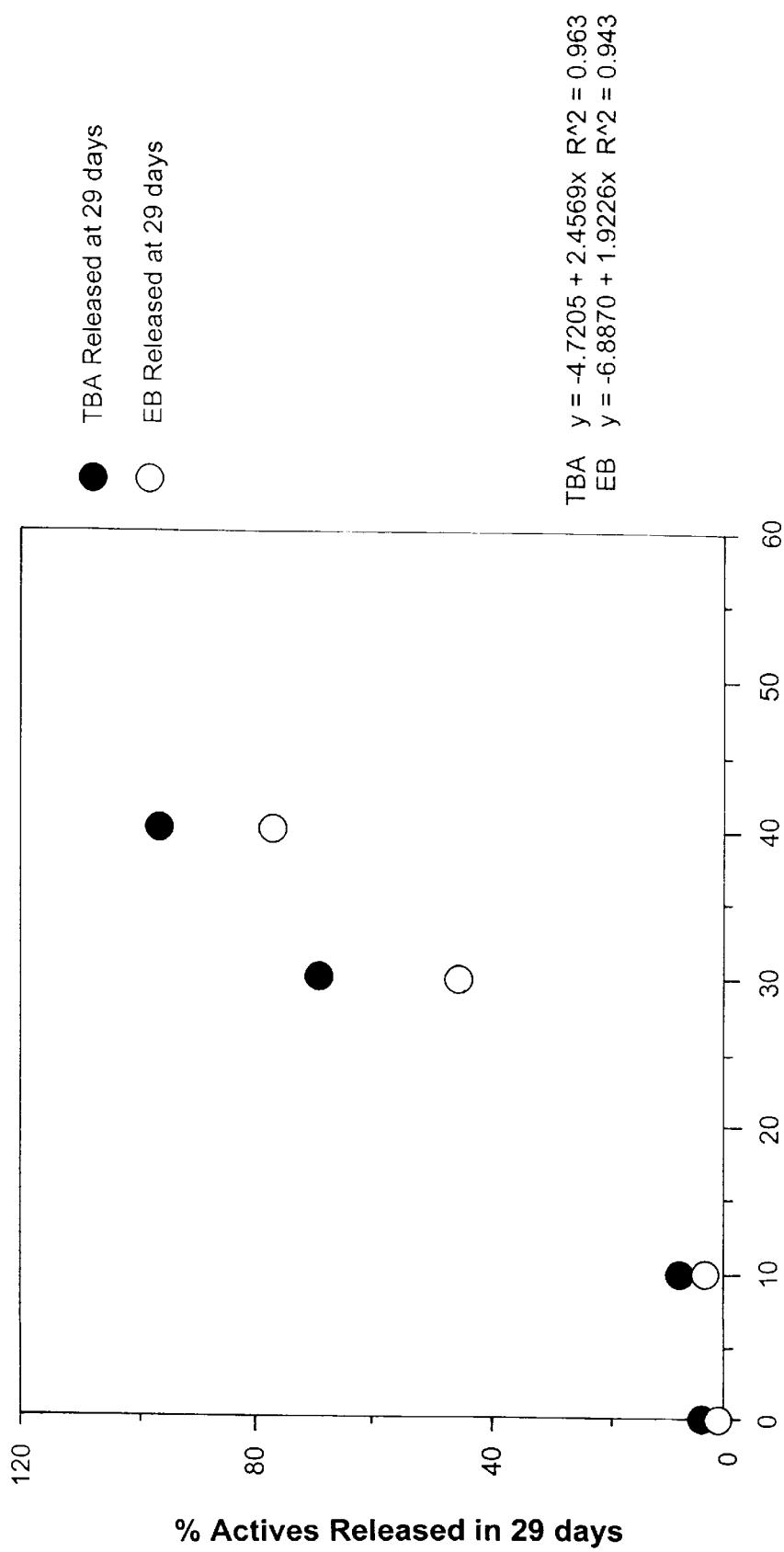
FIG. 4 is a graph showing correlation between the percent of the active agent released and the PEG 8000 concentration.

The amount of pore forming agent incorporated in the film coating formulation affects the release rate of the actives—the more PEG 8000 in the coating formulation, the faster release of the actives. There is a good correlation between the TBA and EB release rates and the amount of PEG 8000 in the formulation as shown in FIG. 4. Within the PEG concentration range between 25–40% the correlation was linear.

In vitro Short Term Dissolution Release Rate Study

The TBA and EB dissolution rates for implants coated with test film formulations were determined in vitro. Six coating formulations (formulations A to F in Table A) were used for this study. As indicated in Table A, the coating formulations consisted of aqueous polymer dispersions (such as Aquacoat ECD 30 or Eudragit RS 30D) mixed with PEG 8000 as a pore forming agent. The concentration of PEG 8000 was in the range from 25–30%. A thin coat comprising 5% and a medium thick coat comprising 10% by weight of an implant were also tested to evaluate the integrity of the coating film during the period of TBA and EB dissolution.

Dissolution rate was monitored for five days using a standard USP dissolution apparatus. The dissolution media was 3% bile salt in purified water. The paddle speed was adjusted at 50 rpm and the bath temperature was set at 37° C.

Samples were collected at hourly intervals as indicated in Table 3 and analyzed using HPLC. The HPLC operating conditions were as indicated above for the "In vitro Long Term Release Rate Study."

The data collected in this study, represented in Table 3, indicate that the release rate for both actives can be regulated by adjusting the coating composition.

The 10% and 15% coatings with 30% PEG 8000 had very similar dissolution profiles for both TBA and EB throughout the 5-day testing. The dissolution rate was slower for Eudragit RS 30D-coated implants than for Aquacoat ECD 30-coated implants at the same amount of PEG 8000 (30%). This difference can be attributed to the elasticity of the acrylic/methacrylic copolymer.

TABLE 3

DISSOLUTION TEST OF VARIOUS TBA/EB LONG ACTING
PREPARATIONS USING A STANDARD USP DISSOLUTION APPARATUS

| | | | | TIME (HOURS) | | | | | | |
|---|---|---|---|---|---|---|---|---|---|---|
| F# | COATING POLYMER | % PEG | % COAT | 5 | 22 | 30 | 46 | 70 | 94 | 120 |
| PERGENT TBA DISSOLVED | | | | | | | | | | |
| A | AQUACOAT ® ECD 30 | 25.0 | 10.0 | 1.28 | 2.37 | 2.74 | 3.83 | 5.31 | 7.05 | 9.01 |
| B | AQUACOAT ® ECD 30 | 30.0 | 10.0 | 1.29 | 2.93 | 3.55 | 5.18 | 7.19 | 9.29 | 11.75 |
| C | AQUACOAT ® ECD 30 | 35.0 | 10.0 | 1.49 | 3.75 | 4.82 | 7.33 | 11.06 | 15.50 | 19.60 |
| D | AQUACOAT ® ECD 30 | 40.0 | 10.0 | 1.67 | 4.94 | 6.70 | 10.42 | 15.71 | 21.08 | 27.30 |

TABLE 3-continued

DISSOLUTION TEST OF VARIOUS TBA/EB LONG ACTING
PREPARATIONS USING A STANDARD USP DISSOLUTION APPARATUS

| | | | | TIME (HOURS) | | | | | |
|---|---|---|---|---|---|---|---|---|---|
| F# COATING POLYMER | % PEG | % COAT | 5 | 22 | 30 | 46 | 70 | 94 | 120 |
| E EUDRAGIT ® RS 30D | 30.0 | 10.0 | 1.01 | 1.35 | 1.91 | 3.14 | 4.87 | 6.93 | 8.82 |
| F AQUACOAT ® ECD 30 | 35.0 | 15.0 | 1.28 | 2.79 | 3.28 | 4.43 | 6.28 | 7.77 | 9.78 |
| DISSOLUTION RATE OF TBA (MG/HOUR) | | | | | | | | | |
| A AQUACOAT ® ECD 30 | 25.0 | 10.0 | 0.51 | 0.13 | 0.09 | 0.14 | 0.12 | 0.15 | 0.15 |
| B AQUACOAT ® ECD 30 | 30.0 | 10.0 | 0.52 | 0.19 | 0.16 | 0.21 | 0.17 | 0.18 | 0.19 |
| C AQUACOAT ® ECD 30 | 35.0 | 10.0 | 0.61 | 0.27 | 0.27 | 0.31 | 0.31 | 0.37 | 0.32 |
| D AQUACOAT ® ECD 30 | 40.0 | 10.0 | 0.67 | 0.38 | 0.44 | 0.47 | 0.44 | 0.45 | 0.48 |
| E EUDRAGIT ® RS 30D | 30.0 | 10.0 | 0.40 | 0.04 | 0.14 | 0.15 | 0.14 | 0.17 | 0.15 |
| F AQUACOAT ® ECD 30 | 35.0 | 15.0 | 0.51 | 0.18 | 0.12 | 0.14 | 0.15 | 0.12 | 0.15 |

Figure 5:
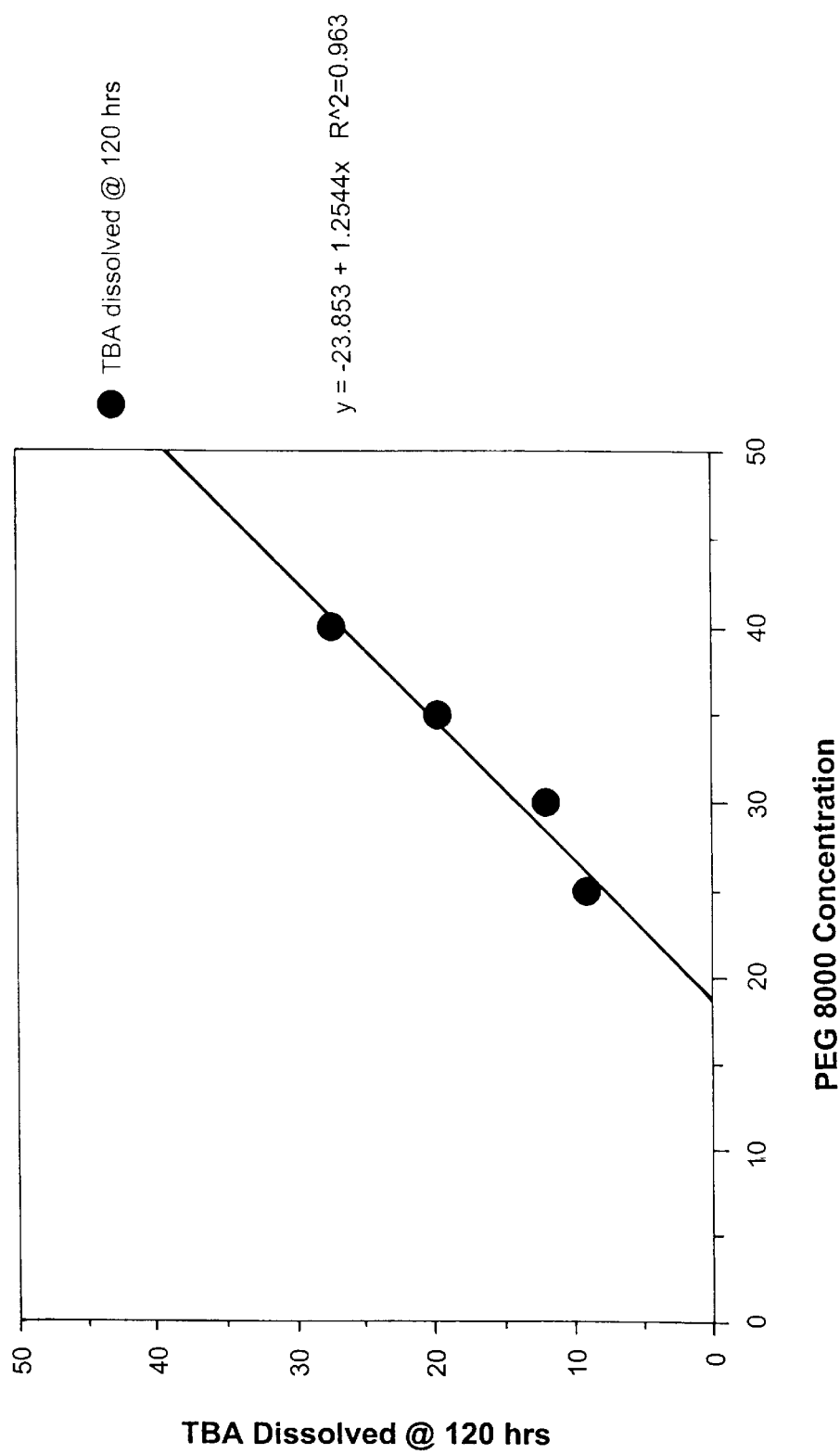
FIG. 5 is a graph showing correlation between the percent of TBA released and the PEG 8000 concentration.
Figure 6:
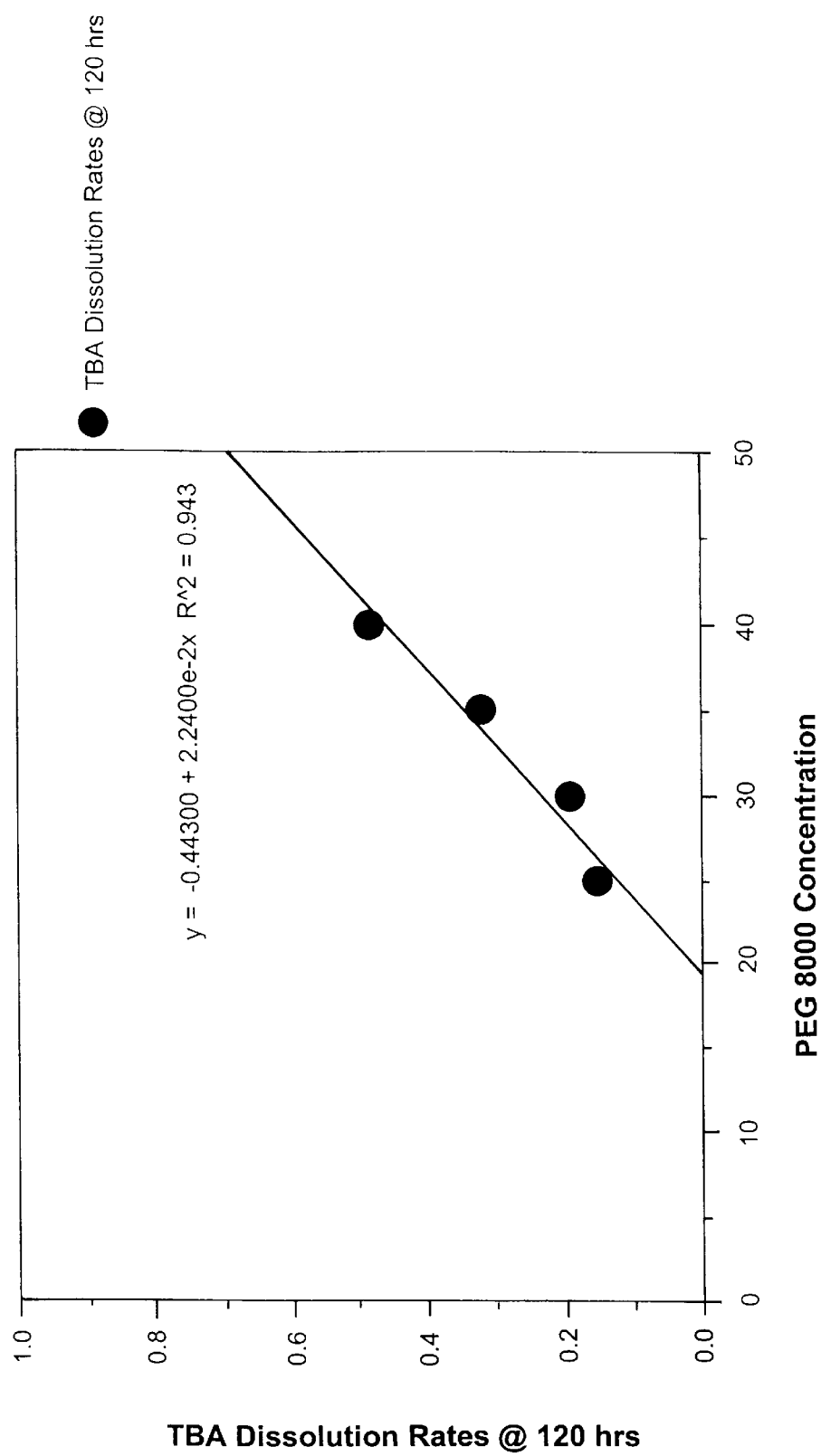
FIG. 6 is a graph showing correlation between TBA dissolution rates (during a period of 30 days in a reciprocating apparatus) and the PEG 8000 concentration.
Figure 7B:
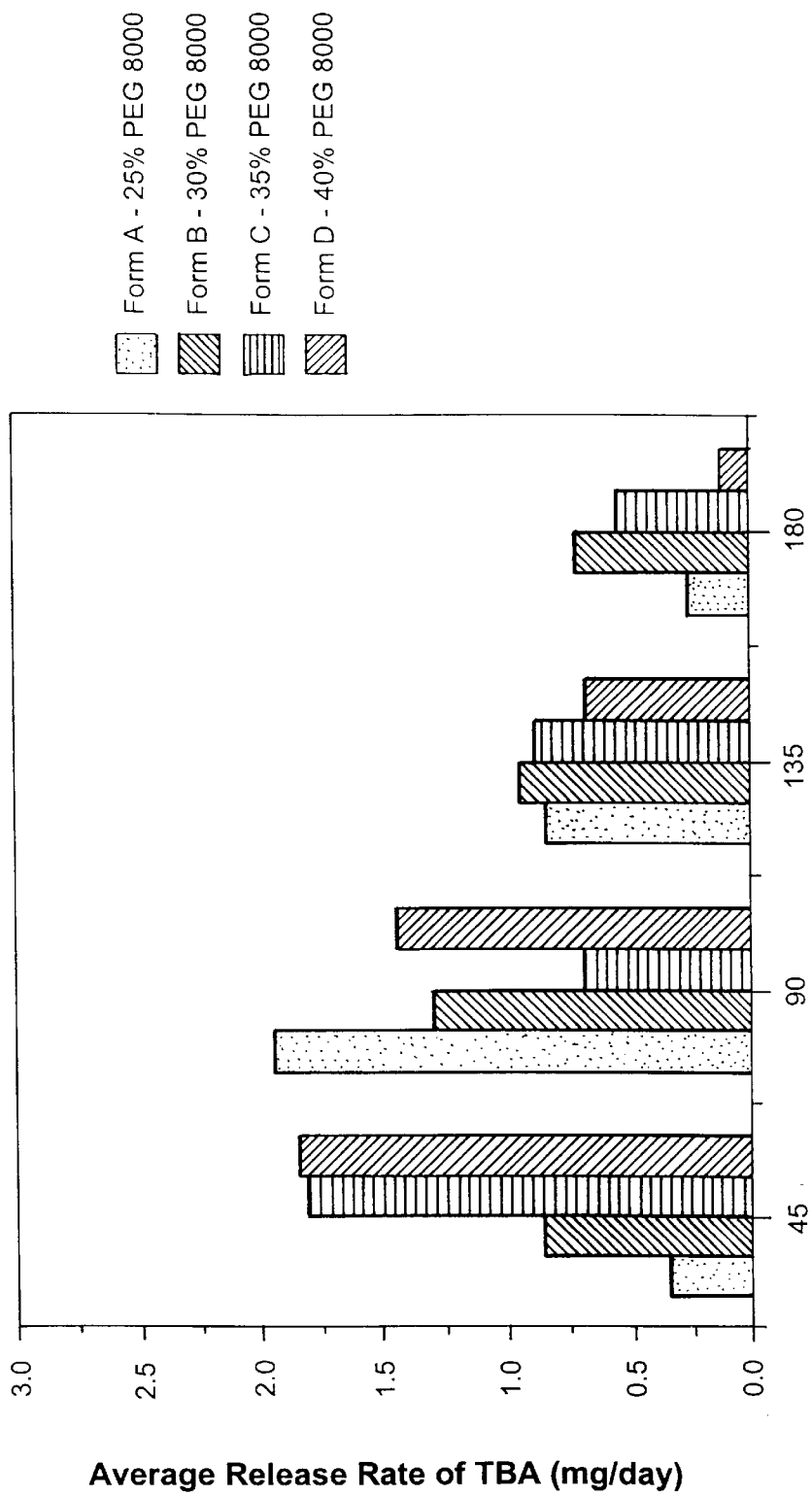
FIG. 7b is a graph showing TBA depletion (represented by an average release rate mg/day) depending on varying PEG 8000 concentrations.
Figure 7D:
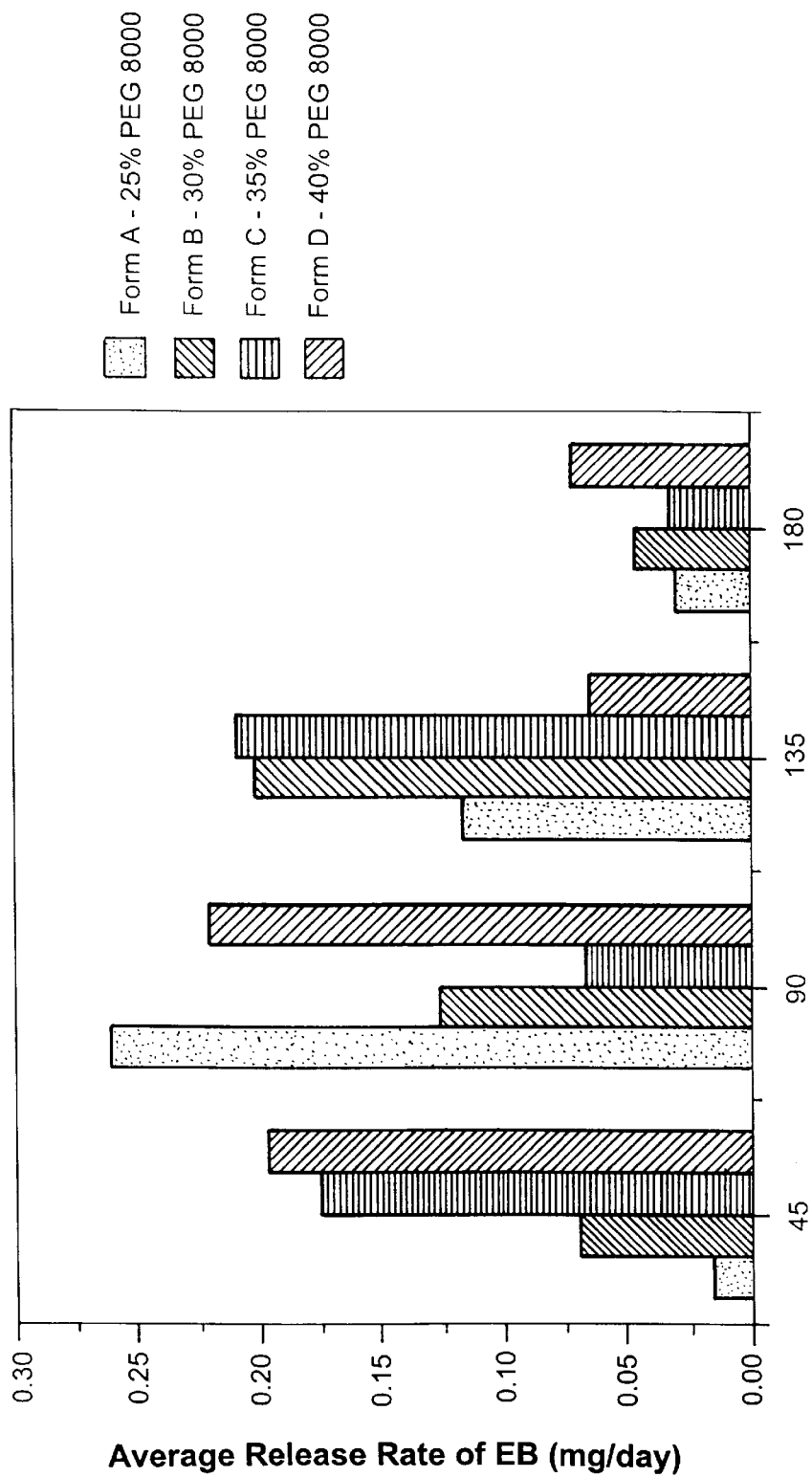
FIG. 7d is a graph showing EB depletion (represented by an average release rate mg/day) depending on varying PEG 8000 concentrations.

Dissolution rate of the actives and the amount of PEG 8000 incorporated in the coating formulations shows a very good correlation. FIGS. 5 and 6 illustrate this correlation.

In vivo Animal Study

The TBA and EB release in vivo was determined using 24 steers. Pellets containing TBA and EB were coated with six film formulations designated as formulations A to F in Table A and injected subcutaneously in the ears of test steers. Each animal received 6 implants (three in each ear), one of each formulation A to F. The total duration of the study was 180 days and implants were excised and removed at four time points, at day 45, 90, 135 and 180. Six implants per each formulation (from six animals) were removed at each time interval.

Removed samples were analyzed for residual TBA and EB. Each sample and the residual tissue was transferred to a 100 ml volumetric flask. Samples were sonicated with methanol for 20 minutes, then filtered using Acrodisc LC-13 HPLC filter. Samples were then analyzed using an HPLC method operated with the conditions described above.

The percent actives remaining and depletion rate of the actives are represented in Tables 4 and 5. The in vivo depletion findings were similar to the results obtained in the in vitro dissolution study. The formulations with higher concentrations of PEG 8000 depleted faster than those with lower PEG concentration. FIGS. 7a–7d demonstrate this effect and confirm the conclusions obtained from in vitro studies.

Figure 8A:
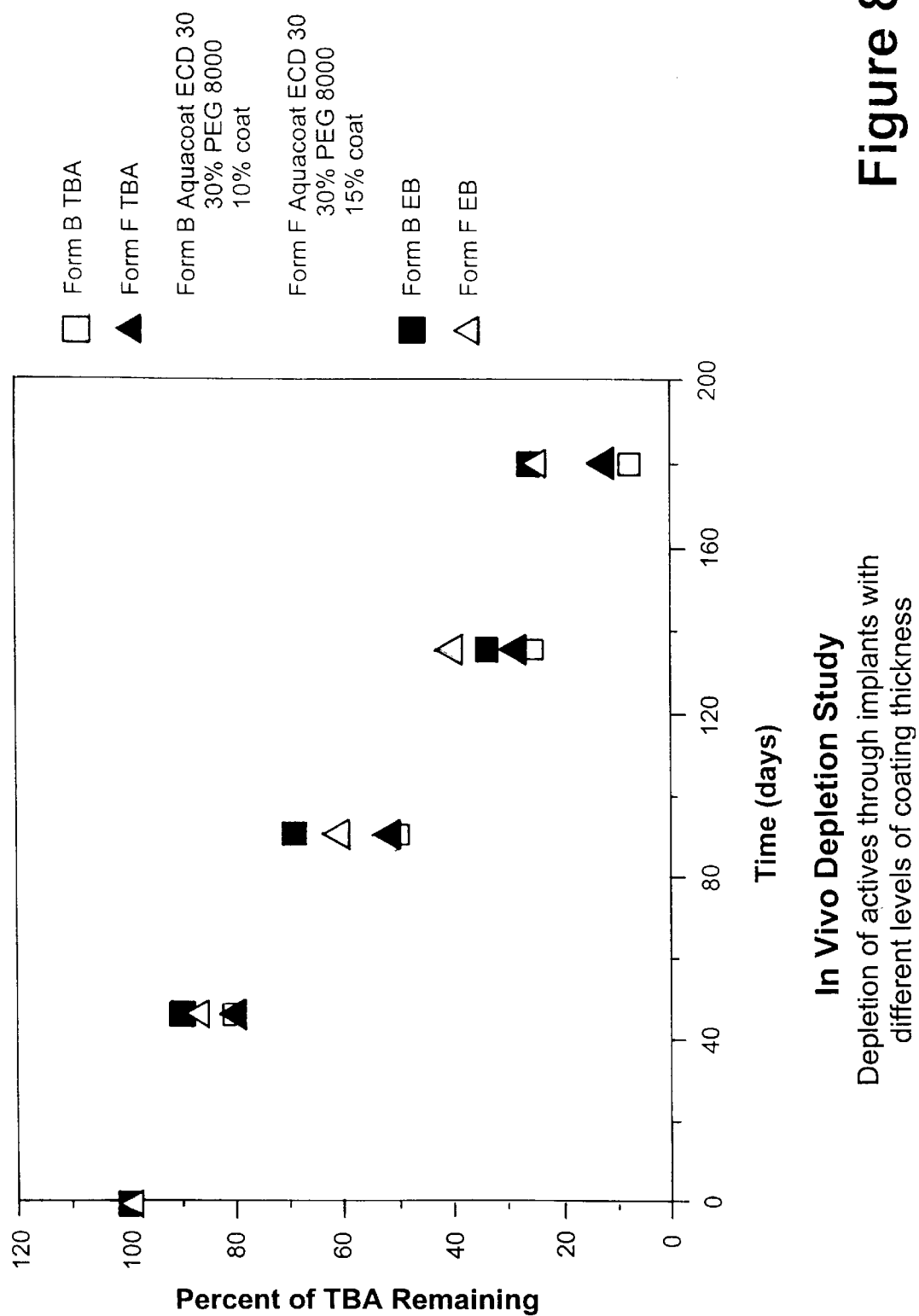
FIG. 8a is a graph showing depletion of actives (represented by percent active remaining in the implant) depending on the coating thickness.
Figure 8B:
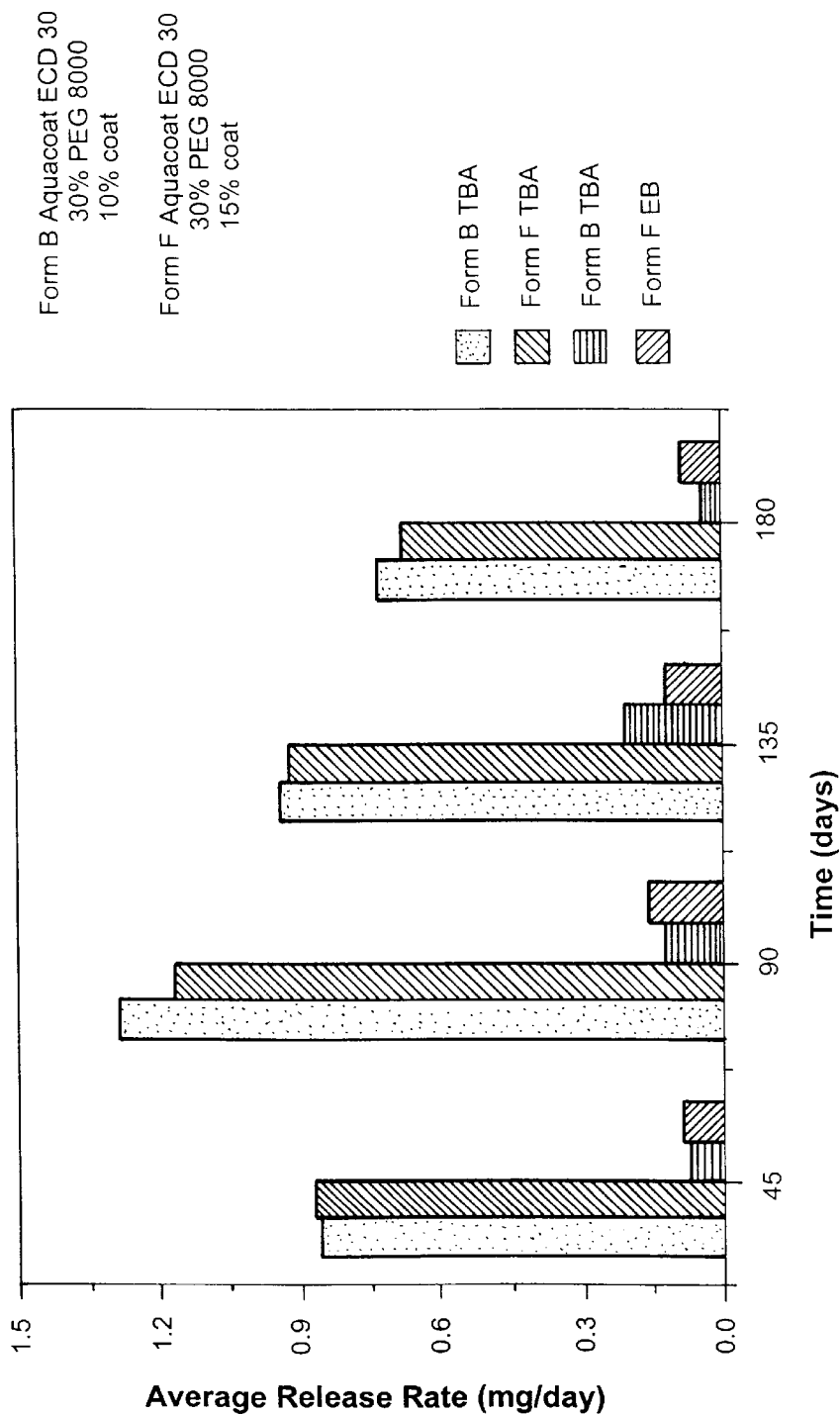
FIG. 8b is a graph showing depletion of actives (represented by average release rate mg/day) depending on the coating thickness.

Thickness (10 and 15% coating) did not affect the release of the actives but did add consistency to the release rates for the entire implantation period. FIGS. 8a and 8b show release profiles for implants with different levels of coating.

Eudragit RS 30D formulation showed a slower release rate for both actives in comparison to Aquacoat formulations containing the same amount of PEG 8000. This is illustrated in FIG. 9a. It is noted that, the Aquacoat coated pellets with 25% PEG had a much higher depletion rate at day 90 than expected. However, this may be due to a burst in the film caused by the high osmotic pressure generated inside the capsule during the earlier implantation stage.

At day 180, about 5–20% of TBA and 10–30% of EB were recovered from test implants. Aquacoat coated implants with 30% or 35% PEG showed the most desired release pattern, i.e., the longest duration of release.

Figure 10:
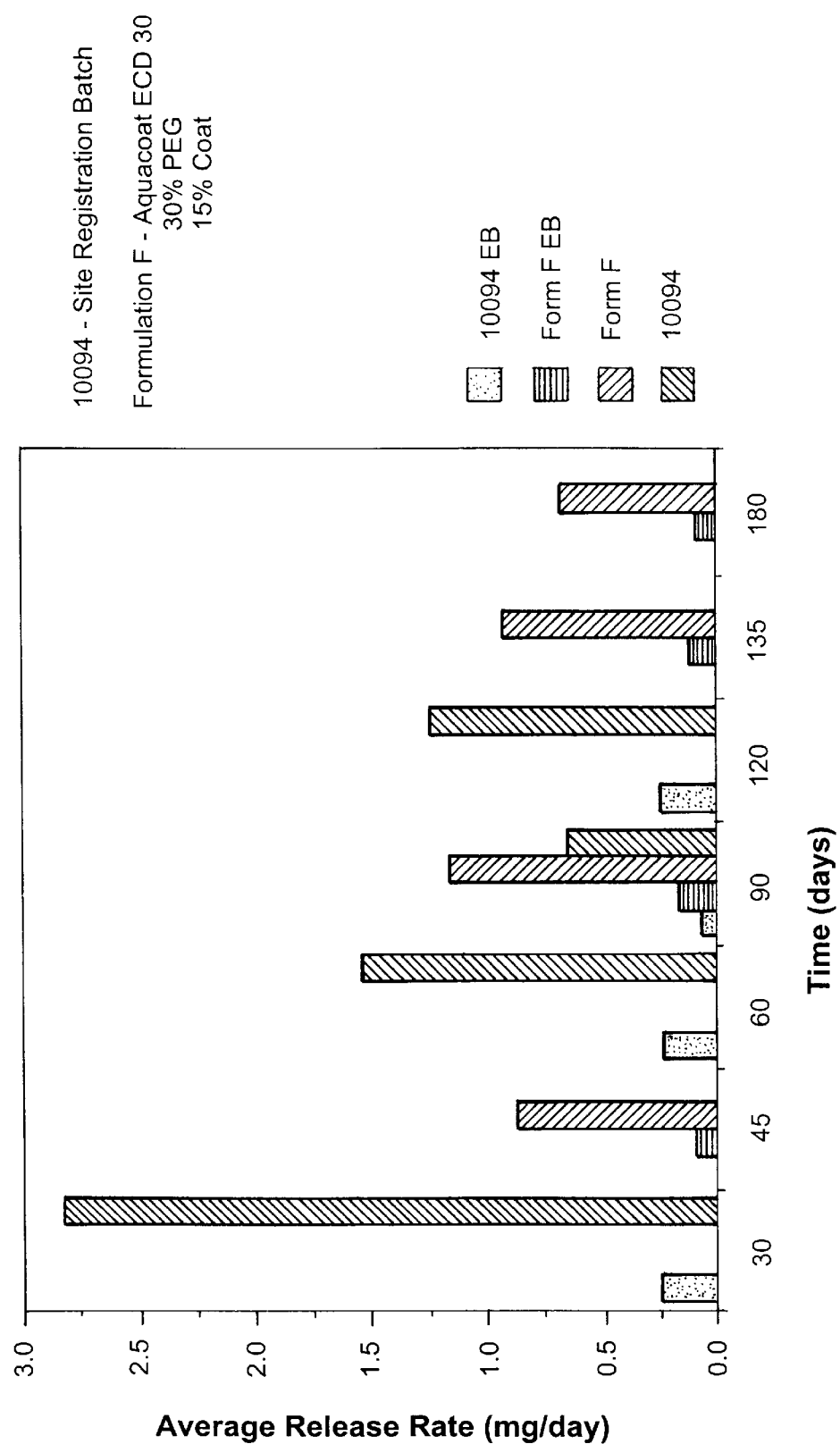
FIG. 10 is a graph showing a comparison of the release rates (represented by the average release rate mg/day) of TBA/EB implants currently available on the market and TBA/EB implants prepared according to the present invention.

FIG. 10 shows the comparison of the release rates from the current TBA/EB implant and the coated implants with Aquacoat ECD 30, 30% PEG and 15% overall coating. These results establish that the duration of the current TBA/EB implants can be prolonged beyond 180 days by using the coating formulation of the present invention.

In vitro and in vivo correlations

Figure 11:
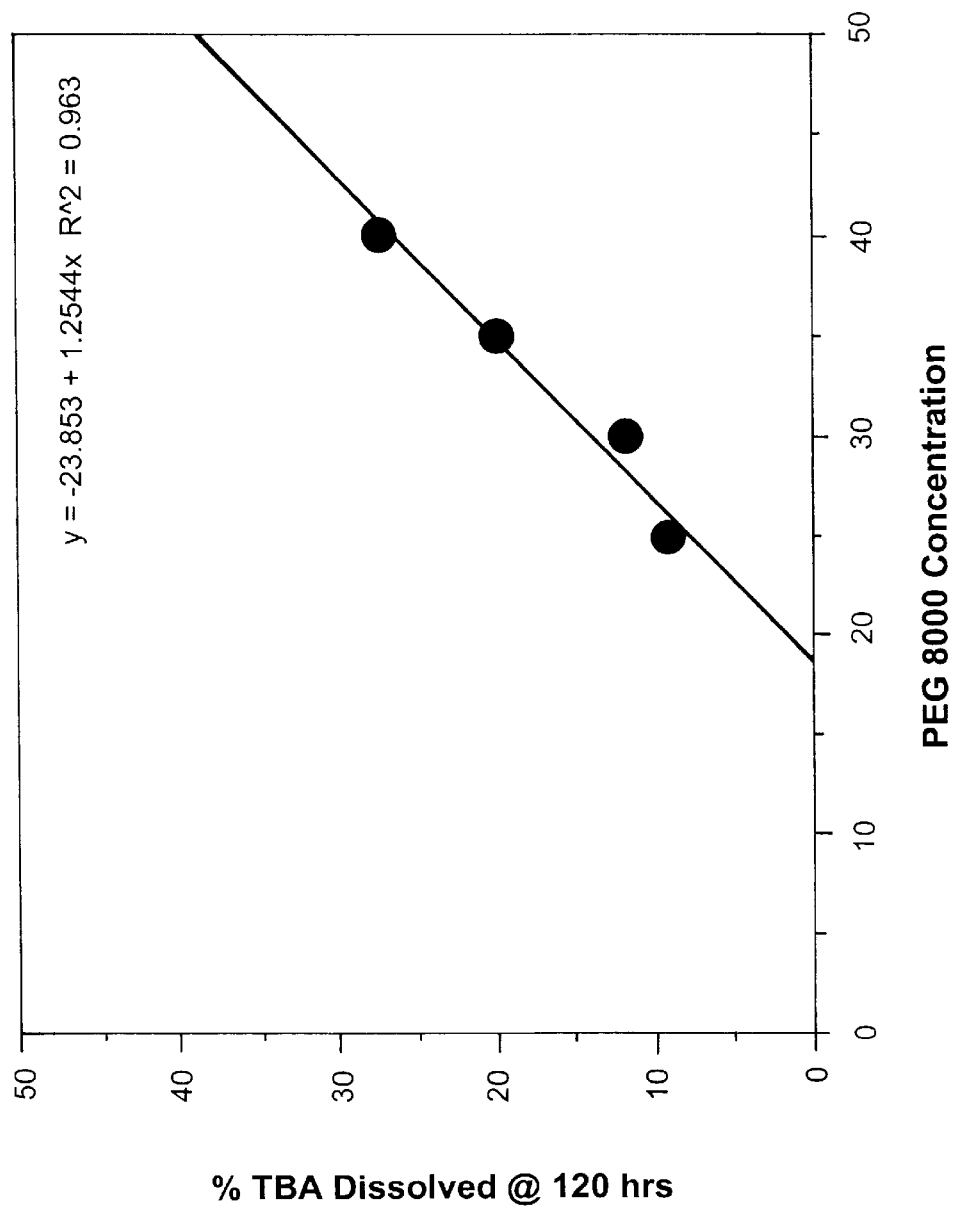
FIG. 11 is a graph showing correlation between the percent of TBA dissolved in vitro after 120 hours and the concentration of PEG 8000 in the coating.
Figure 12:
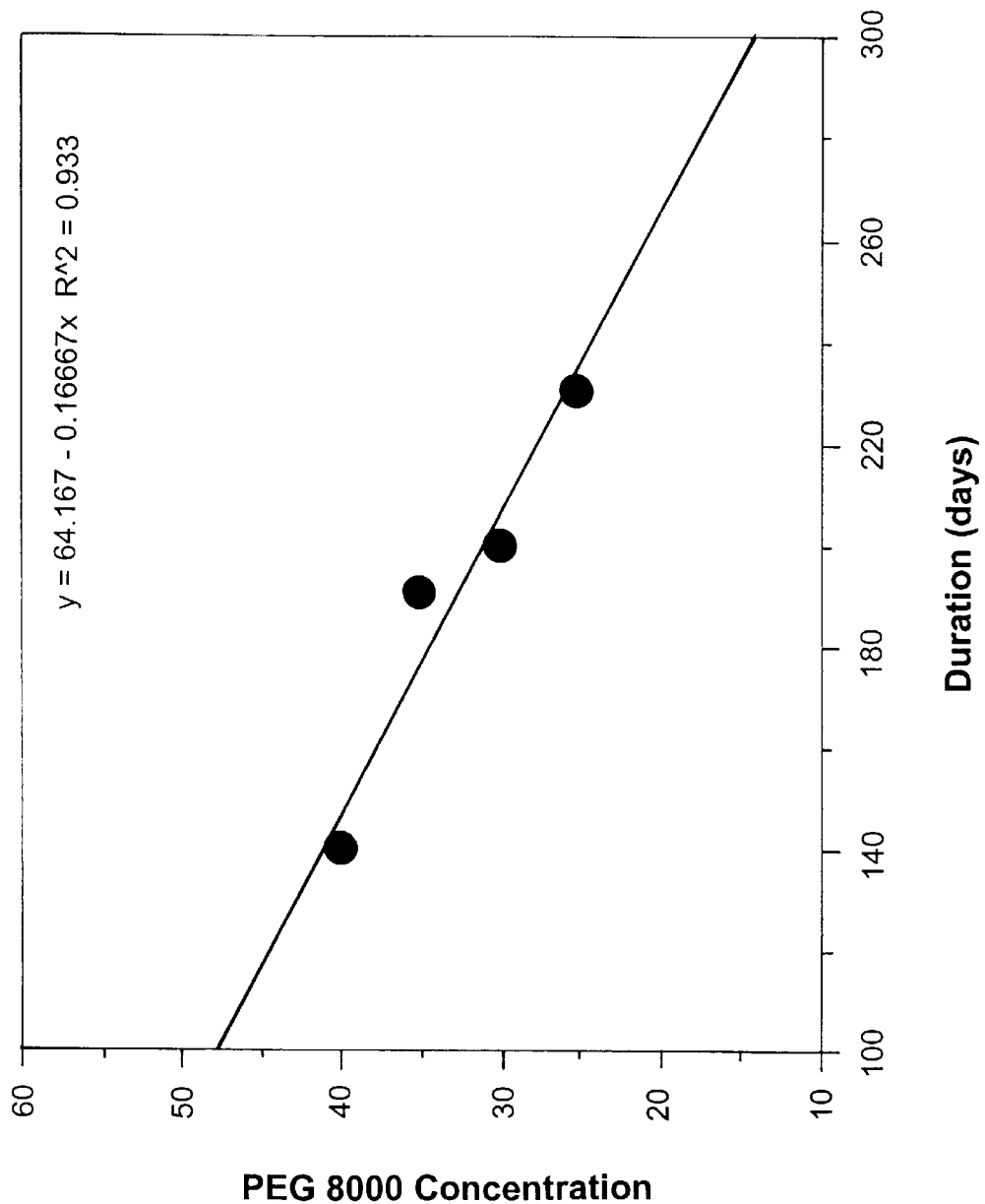
FIG. 12 is a graph showing correlation between the concentration of PEG 8000 in the coating and the lifetime of the implant.

The effect of the PEG 8000 concentration in the coating formulation on the in vitro dissolution rates of TBA (%) is shown in FIG. 11. Also, a correlation between the extrapolated in vivo duration of the implants and the concentration (%) of PEG 8000 in the coating film is shown in FIG. 12. From the correlation, the most desirable coating formulation to obtain a 200-day implant duration comprises Aquacoat ECD 30, approximately 32% PEG and at least 15% overall coating by weight.

Figure 13:
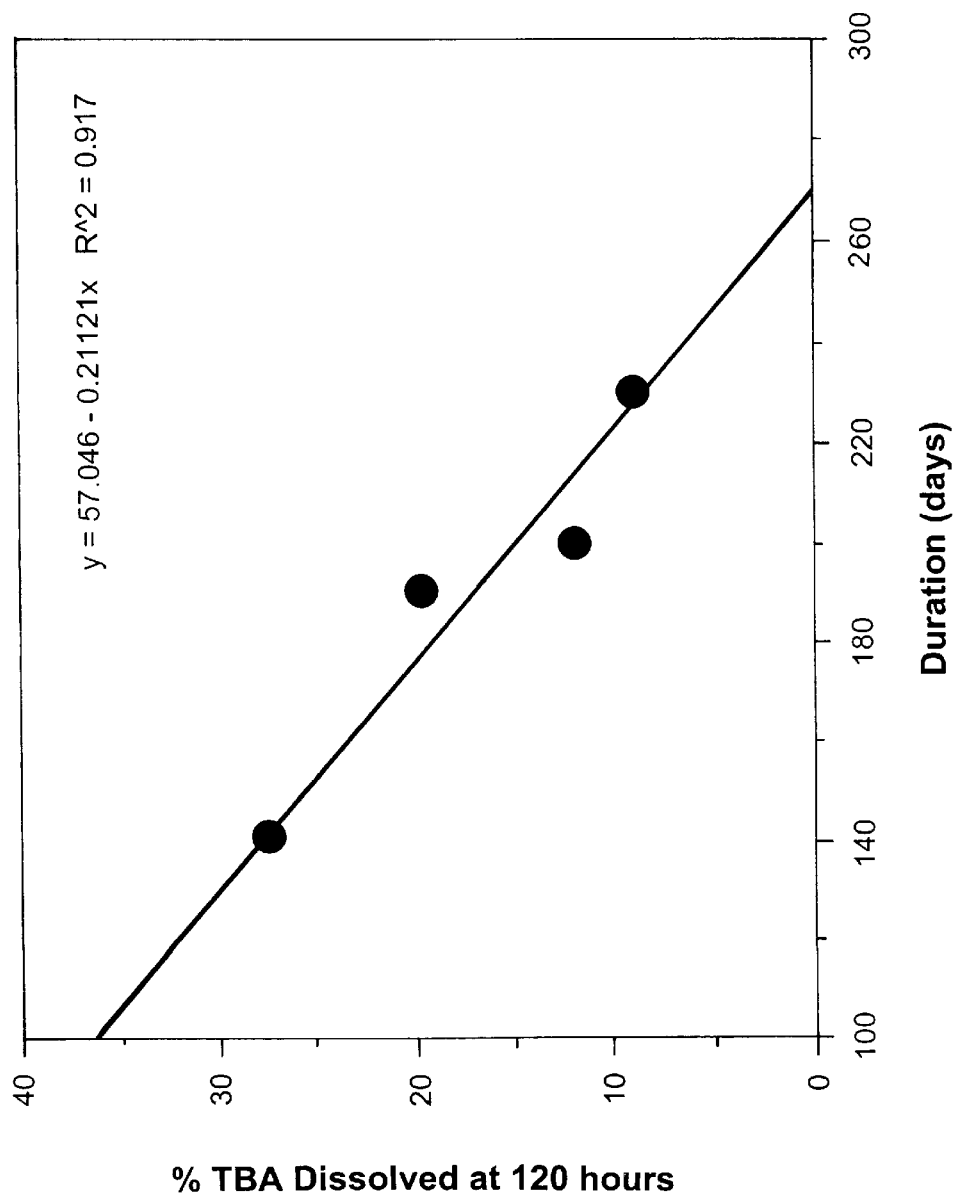
FIG. 13 is a graph showing correlation between the lifetime duration of an implant and the percent of TBA dissolved in vitro after 120 hours.

Finally, the possibility of using in vitro dissolution rates of coated implants obtained at the 120-hour time point to predict in vivo duration of the coated implants was investigated. A good correlation was observed as shown in FIG. 13.

TABLE 4

IN VIVO DEPLETION OF VARIOUS TBA/EB LONG ACTING PREPARATIONS IN STEERS

| | | | | IMPLANTATION PERIOD (DAYS) | | | | | |
|---|---|---|---|---|---|---|---|---|---|
| F# COATING POLYMER | % PEG | % COAT | 45 | (S.D.) | 90 | (S.D.) | 135 | (S.D.) | 180 | (S.D.) |
| PERCENT TBA REMAINING | | | | | | | | | | |
| A AQUACOAT ® ECD 30 | 25.0 | 10.0 | 91.68 | 4.57 | 44.48 | 24.39 | 24.78 | 14.40 | 18.37 | 13.43 |
| B AQUACOAT ® ECD 30 | 30.0 | 10.0 | 80.83 | 8.96 | 49.61 | 20.62 | 25.24 | 23.24 | 7.67 | 6.48 |
| C AQUACOAT ® ECD 30 | 35.0 | 10.0 | 58.68 | 8.91 | 40.00 | 7.12 | 18.76 | 17.06 | 5.65 | 3.55 |
| D AQUACOAT ® ECD 30 | 40.0 | 10.0 | 56.44 | 6.05 | 21.79 | 12.57 | 5.31 | 6.61 | 2.60 | 4.76 |
| E EUDRAGIT ® RS 30D | 30.0 | 10.0 | 94.21 | 4.49 | 64.18 | 16.84 | 31.46 | 17.79 | 11.01 | 7.84 |
| F AQUACOAT ® ECD 30 | 35.0 | 15.0 | 80.52 | 3.97 | 51.99 | 9.21 | 28.97 | 20.28 | 12.85 | 12.76 |

TABLE 4-continued

IN VIVO DEPLETION OF VARIOUS TBA/EB LONG ACTING PREPARATIONS IN STEERS

| F# | COATING POLYMER | % PEG | % COAT | 45 | (S.D.) | 90 | (S.D.) | 135 | (S.D.) | 180 | (S.D.) |
|---|---|---|---|---|---|---|---|---|---|---|---|
| PERCENT EB REMAINING | | | | | | | | | | | |
| A | AQUACOAT ® ECD 30 | 25.0 | 10.0 | 96.82 | 5.51 | 54.05 | 26.57 | 34.69 | 16.29 | 29.73 | 17.33 |
| B | AQUACOAT ® ECD 30 | 30.0 | 10.0 | 89.84 | 8.37 | 69.24 | 22.50 | 33.61 | 29.50 | 25.92 | 15.56 |
| C | AQUACOAT ® ECD 30 | 35.0 | 10.0 | 73.78 | 9.58 | 60.52 | 8.24 | 26.33 | 16.40 | 20.96 | 5.63 |
| D | AQUACOAT ® ECD 30 | 40.0 | 10.0 | 67.19 | 11.04 | 30.41 | 14.91 | 19.59 | 25.85 | 7.67 | 9.45 |
| E | EUDRAGIT ® RS 30D | 30.0 | 10.0 | 94.90 | 4.97 | 74.96 | 20.13 | 41.82 | 17.89 | 26.87 | 13.77 |
| F | AQUACOAT ® ECD 30 | 35.0 | 15.0 | 87.68 | 4.91 | 61.44 | 11.45 | 40.29 | 21.93 | 25.49 | 25.49 |

TABLE 5

IN VIVO DEPLETION OF VARIOUS TBA/EB LONG ACTING PREPARATIONS IN STEERS

| F# | COATING POLYMER | % PEG | % COAT | 45 | 90 | 135 | 180 |
|---|---|---|---|---|---|---|---|
| TBA DEPLETION RATE (MG/DAY) | | | | | | | |
| A | AQUACOAT ® ECD 30 | 25.0 | 10.0 | 0.345 | 1.945 | 0.835 | 0.266 |
| B | AQUACOAT ® ECD 30 | 30.0 | 10.0 | 0.854 | 1.287 | 0.938 | 0.724 |
| C | AQUACOAT ® ECD 30 | 35.0 | 10.0 | 1.808 | 0.701 | 0.887 | 0.547 |
| D | AQUACOAT ® ECD 30 | 40.0 | 10.0 | 1.836 | 1.432 | 0.681 | 0.112 |
| E | EUDRAGIT ® RS 30D | 30.0 | 10.0 | 0.384 | 1.113 | 1.393 | 0.828 |
| F | AQUACOAT ® ECD 30 | 35.0 | 15.0 | 0.871 | 1.165 | 0.921 | 0.673 |
| EB DEPLETION RATE (MG/DAY) | | | | | | | |
| A | AQUACOAT ® ECD 30 | 25.0 | 10.0 | 0.015 | 0.261 | 0.117 | 0.029 |
| B | AQUACOAT ® ECD 30 | 30.0 | 10.0 | 0.071 | 0.126 | 0.202 | 0.046 |
| C | AQUACOAT ® ECD 30 | 35.0 | 10.0 | 0.175 | 0.066 | 0.209 | 0.033 |
| D | AQUACOAT ® ECD 30 | 40.0 | 10.0 | 0.196 | 0.220 | 0.065 | 0.072 |
| E | EUDRAGIT ® RS 30D | 30.0 | 10.0 | 0.058 | 0.094 | 0.208 | 0.086 |
| F | AQUACOAT ® ECD 30 | 35.0 | 15.0 | 0.084 | 0.156 | 0.122 | 0.090 |

What is claimed is:

1. A long term sustained-release implant comprising:
   (i) an effective amount of a biologically active agent; and
   (ii) a film coat comprising a mixture of a water insoluble polymer and a polyethylene glycol as a water soluble pore forming agent, said polyethylene glycol being in an amount effective to regulate the release of said biologically active compound, wherein the duration of sustained release of the implant in a mammal is greater than 100 days.

2. The implant of claim 1 wherein the molecular weight of said polyethylene glycol is from about 200 to about 20,000.

3. The implant of claim 1 wherein the molecular weight of said polyethylene glycol is about 8,000.

4. The implant of claim 1 wherein said effective amount of said polyethylene glycol is from about 10% to about 50% per dry weight of said film coat.

5. The implant of claim 1 wherein said water insoluble polymer is cellulose ethyl ether, or poly(ethylacrylate, methylmethacrylate, trimethylammonioethyl-methacrylate).

6. The implant of claim 1 wherein said biologically active compound is a steroid hormone.

7. The implant of claim 6 wherein said steroid hormone comprises an estrogen derivative in combination with a progestogen, and androgen or a combination thereof.

8. The implant of claim 1 wherein said biologically active compound is a steroid hormone in an amount effective to promote livestock weight gain and said polyethylene glycol has the molecular weight of about 8,000 and is present in the amount of between 10% to 50% per dry weight of the coating film.

9. The implant of claim 8 wherein the thickness of said film coat is between 5 to 50 μm.

10. The implant of claim 8 wherein said steroid hormone is estradiol benzoate and trenbolone acetate.

11. A method for treating a mammal comprising implanting into the body of said mammal a long term sustained-release implant comprising:
   (i) an effective amount of a biologically active agent; and
   (i) a film coat comprising a mixture of a water insoluble polymer and a polyethylene glycol as a water soluble pore forming agent, said polyethylene glycol being in an amount effective to regulate the release of said biologically active compound, wherein duration of sustained release of the implant in the mammal is greater than 100 days.

12. The method of claim 11 wherein the molecular weight of said polyethylene glycol is from about 200 to about 20,000.

13. The method of claim 11 wherein the molecular weight of said polyethylene glycol is about 8,000.

14. The method of claim 11 wherein said effective amount of said polyethylene glycol is from about 10% to about 50% per dry weight of said film coat.

15. The method of claim 11 wherein said water insoluble polymer is cellulose ethyl ether or poly(ethylacrylate, methylmethacrylate, trimethylammonioethyl-methacrylate).

16. The method of claim 11 wherein said biologically active compound is a steroid hormone.

17. The method of claim 16 wherein said steroid hormone comprises an estrogen derivative in combination with a progestogen, and androgen or a combination thereof.

18. The method of claim 11 wherein said biologically active compound is a steroid hormone in an amount effective to promote livestock weight gain and said polyethylene glycol has the molecular weight of about 8,000 and is present in the amount of between 10% to 50% per dry weight of the film coat.

19. The method of claim 18 wherein the thickness of said film coat is between 5 to 50 $\mu$m.

20. The method of claim 18 wherein said steroid hormone is estradiol benzoate and trenbolone acetate.

21. A long term sustained-release implant comprising:
(i) an effective amount of a biologically active agent; and
(ii) a film coat comprising a mixture of a water insoluble polymer and a water soluble pore forming agent, said pore forming agent being in an amount effective to regulate the release of said biologically active compound, wherein the duration of sustained release of the implant in a mammal is greater than 150 days.

22. The implant of claim 21 wherein said water soluble pore forming agent is polyethylene glycol, polypropylene glycol, sugar, salt, poloxamers, or polyvinyl alcohol.

* * * * *